(12) United States Patent
Gysling

(10) Patent No.: US 7,299,705 B2
(45) Date of Patent: Nov. 27, 2007

(54) APPARATUS AND METHOD FOR AUGMENTING A CORIOLIS METER

(75) Inventor: Daniel L. Gysling, Glastonbury, CT (US)

(73) Assignee: CiDRA Corporation, Wallingford, CT (US)

( * ) Notice: Subject to any disclaimer, the term of this patent is extended or adjusted under 35 U.S.C. 154(b) by 61 days.

(21) Appl. No.: 11/291,189

(22) Filed: Nov. 30, 2005

(65) Prior Publication Data

US 2006/0169058 A1   Aug. 3, 2006

Related U.S. Application Data

(63) Continuation-in-part of application No. 10/892,886, filed on Jul. 15, 2004, now Pat. No. 7,152,460.

(60) Provisional application No. 60/631,793, filed on Nov. 30, 2004, provisional application No. 60/579,448, filed on Jun. 14, 2004, provisional application No. 60/570,321, filed on May 12, 2004, provisional application No. 60/539,640, filed on Jan. 28, 2004, provisional application No. 60/524,964, filed on Nov. 25, 2003, provisional application No. 60/512,794, filed on Oct. 20, 2003, provisional application No. 60/510,302, filed on Oct. 10, 2003, provisional application No. 60/504,785, filed on Sep. 22, 2003, provisional application No. 60/503,334, filed on Sep. 16, 2003, provisional application No. 60/491,860, filed on Aug. 1, 2003, provisional application No. 60/487,832, filed on Jul. 15, 2003.

(51) Int. Cl.
G01F 1/66    (2006.01)
G01F 1/84    (2006.01)

(52) U.S. Cl. ............................. 73/861.27; 73/861.354

(58) Field of Classification Search ............... 73/61.44, 73/64.45, 64.47, 61.49, 61.78, 61.79, 861.04, 73/861.08, 32 A, 861.18, 861.27, 861.351, 73/861.354
See application file for complete search history.

(56) References Cited

U.S. PATENT DOCUMENTS 4,262,523 A * 4/1981 Stansfeld ................ 73/24.05
4,823,613 A * 4/1989 Cage et al. ............ 73/861.355
(Continued)

FOREIGN PATENT DOCUMENTS

GB            2009931 A *  6/1979

*Primary Examiner*—Hezron Williams
*Assistant Examiner*—John Fitzgerald
(74) *Attorney, Agent, or Firm*—Michael Grillo

(57) ABSTRACT

A flow measuring system is provided that provides at least one of a compensated mass flow rate measurement and a compensated density measurement. The flow measuring system includes a gas volume fraction meter in combination with a coriolis meter. The GVF meter measures acoustic pressures propagating through the fluids to measure the speed of sound $\alpha_{mix}$ propagating through the fluid to calculate at least gas volume fraction of the fluid and/or the reduced natural frequency. For determining an improved density for the coriolis meter, the calculated gas volume fraction and/or reduced frequency is provided to a processing unit. The improved density is determined using analytically derived or empirically derived density calibration models (or formulas derived therefore), which is a function of the measured natural frequency and at least one of the determined GVF, reduced frequency and speed of sound, or any combination thereof. The gas volume fraction (GVF) meter may include a sensing device having a plurality of strain-based or pressure sensors spaced axially along the pipe for measuring the acoustic pressures propagating through the flow.

14 Claims, 20 Drawing Sheets

U.S. PATENT DOCUMENTS

| | | | | |
|---|---|---|---|---|
| 4,972,724 A * | 11/1990 | Ricken | ................... | 73/861.357 |
| 5,048,349 A * | 9/1991 | Wolff | .................... | 73/861.357 |
| 5,224,372 A * | 7/1993 | Kolpak | ...................... | 73/19.03 |
| 5,488,870 A * | 2/1996 | Yoshimura et al. | .... | 73/861.356 |
| 5,594,180 A * | 1/1997 | Carpenter et al. | ..... | 73/861.356 |
| 5,827,977 A * | 10/1998 | Ortiz et al. | .............. | 73/861.42 |
| 6,318,156 B1 * | 11/2001 | Dutton et al. | .............. | 73/61.44 |
| 7,013,715 B2 * | 3/2006 | Dutton et al. | ............... | 73/61.44 |
| 7,040,181 B2 * | 5/2006 | Rieder et al. | .......... | 73/861.357 |
| 7,152,460 B2 * | 12/2006 | Gysling et al. | ............. | 73/32 A |
| 2004/0173010 A1 * | 9/2004 | Gysling et al. | ............. | 73/64.44 |
| 2005/0044929 A1 * | 3/2005 | Gysling et al. | .............. | 73/32 A |
| 2006/0156831 A1 * | 7/2006 | Rieder et al. | .......... | 73/861.356 |
| 2006/0169058 A1 * | 8/2006 | Gysling | ................. | 73/861.355 |

\* cited by examiner

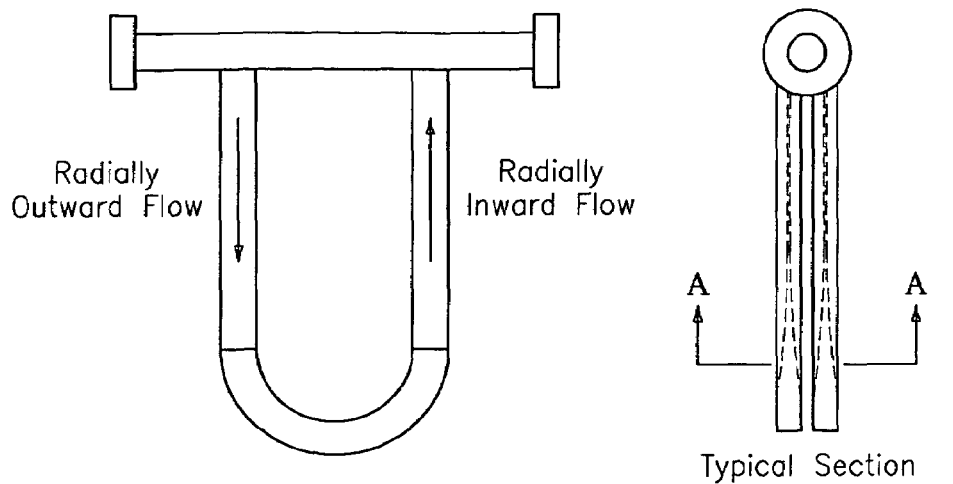
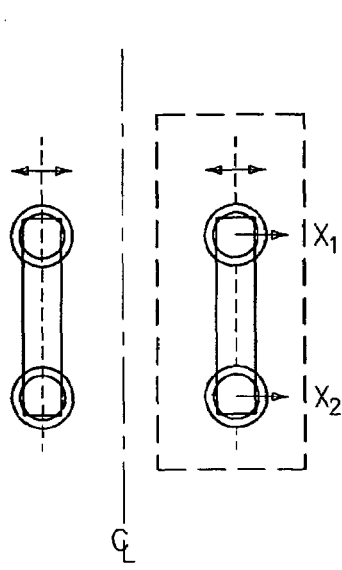
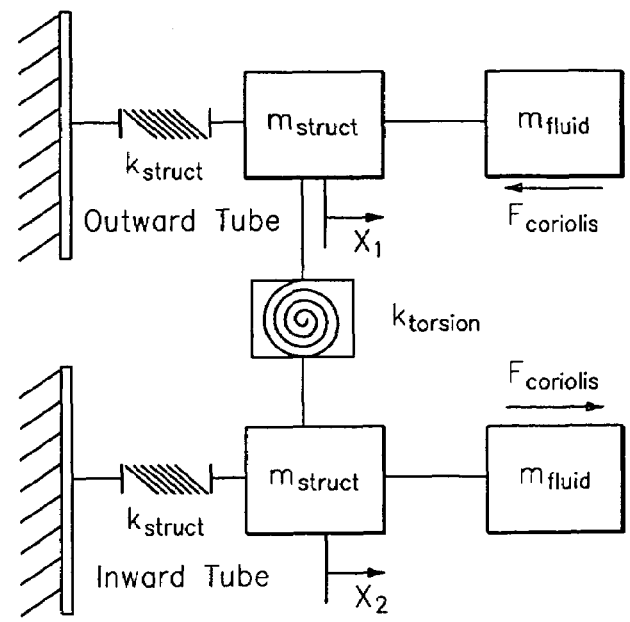
FIG. 4
FIG. 5
FIG. 6
FIG. 7

APPARATUS AND METHOD FOR AUGMENTING A CORIOLIS METER

CROSS-REFERENCE TO RELATED PATENT APPLICATIONS

The present invention claims the benefit of U.S. Provisional Patent Application No. 60/631,793 filed Nov. 30, 2005; and is a continuation-in-part of U.S. patent application Ser. No. 10/892,886 filed Jul. 15, 2004 now U.S. Pat. No. 7,152,460, which claimed the benefit of U.S. Provisional Patent Application No. 60/579,448 filed Jun. 14, 2004, U.S. Provisional Patent Application No. 60/570,321 filed May 12, 2004, U.S. Provisional Patent Application No. 60/539,640 filed Jan. 28, 2004, U.S. Provisional Patent Application No. 60/524,964 filed Nov. 25, 2003, U.S. Provisional Patent Application No. 60/512,794 filed Oct. 20, 2003, U.S. Provisional Patent Application No. 60/510,302 filed Oct. 10, 2003, U.S. Provisional Patent Application No. 60/504,785 filed Sep. 22, 2003, U.S. Provisional Patent Application No. 60/503,334 filed Sep. 16, 2003, U.S. Provisional Patent Application No. 60/491,860 filed Aug. 1, 2003, and U.S. Provisional Patent Application No. 60/487,832 filed Jul. 15, 2003, which are all incorporated herein by reference.

TECHNICAL FIELD

This invention relates to an apparatus for measuring the density and/or mass flow rate of a flow having entrained gas therein, and more particularly to an apparatus that measures the speed of sound propagating through the flow to determine the gas volume fraction of the flow in the process to augment or correct the density and or mass flow rate measurement of a coriolis meter.

BACKGROUND ART

Coriolis mass flow and density meters are considered the flow metering solution of choice for many precision flow applications. Since their introduction to the mainstream flow metering community in the early 1980's, coriolis meters have grown into one of largest and fastest growing market segments, representing roughly $400 million annual sales on approximately 100,000 units. The success of coriolis meters has been attributed to many factors, including its accuracy, reliability, and ability to measure multiple process parameters, including mass flow and process fluid density. However, despite this long list of attributes, coriolis meters have significant limitations regarding aerated liquids. Although the mass flow rate and process fluid density measurements determined by coriolis meters are derived from independent physical principles, the accuracy of both are significantly degraded with the introduction of small amounts of entrained gases. This paper develops and lumped parameter aeroelastic model for coriolis meters operating on aerated fluids. The model is to examine the influence of several key, non-dimensional parameters that influence the effect on aeration on the mass flow and density reported by commercially available coriolis flow meters.

Coriolis meters are widely used for industrial flow measurement, representing one of the largest and fasting growing segments in the industrial flow meter market. Coriolis meters have the reputation for high accuracy and provide mass flow and density as their basic measurements.

Since the technology was first adopted by industry beginning in the 1980's, Coriolis meters have developed the reputation as a high priced, high accuracy meter for use in high value applications—predominately within the chemical processing industry. However, despite their success, Coriolis meters have been plagued by poor performance in two-phase flows, predominately bubbly flows of gas/liquid mixtures.

Coriolis meters have two fundamental issues with aerated or bubbly flows. Firstly, bubbly flows present an operability challenge to coriolis meters. Most coriolis meters use electromagnetic drive actuators to vibrate the flow tube at it natural frequency. The meters rely on the vibrating tubes to generate the corilois forces which causes one leg of the flow tube to lag the other. The corilois forces, and hence phase lag, are ideally proportional to the mass flow through the flow tube. The tubes are typically excited at, or near a resonant frequency, and as such, the excitation forces required to maintain a specified vibration amplitude in the tubes is a strong function of the damping in the system. Single phase mixtures introduce little damping to the vibration of the bent tubes, however, the amount of damping in the system dramatically increases with the introduction of gas bubbles. As a result, more power is required to maintain vibration in the tubes in bubbly flows. Often more power is required than is available, resulting in the "stalling" of the Corilois meter.

Furthermore, coriolis meters often require significant time to adjust for the often rapid changes in flow tube resonant frequencies associated with the onset of bubbly or aerated flows. These time-delays, for which the flow tube is essentially stalled, greatly diminish the utility of coriolis meter in many applications where two phase flow and transient response are important such as batch processed. This stalling problem has been and is currently being address by many manufactures.

Secondly, multiphase flows present an accuracy challenge. The accuracy challenge presented by aerated flow regimes is that many of the fundamental assumptions associated with the principle of operation of Corilois meters become increasingly less accurate with the introduction of aerated flow. The present invention provides a means for improving the accuracy of Coriolis meters operating on all types of fluids, with particular emphasis on enhancing the accuracy for operating on two phase, bubbly flows and mixtures.

SUMMARY OF THE INVENTION

Objects of the present invention include an apparatus having a device for determining the speed of sound propagating within a fluid flow in a pipe to determine the gas volume fraction of a process fluid or flow flowing within a pipe, and augment to improve the accuracy of a density and/or mass flow rate measurement of a coriolis meter.

According to the present invention, a flow measuring system for measuring the mass flow rate of an aerated fluid flowing in a pipe is provided. The flow measuring system includes a meter having a pair of vibrating tubes wherein fluid flows therethrough. The meter provides a phase signal indicative of a phase difference between the pair of tubes. The tubes have an inward flow portion and an outward flow portion. A flow measuring device measuring the speed of sound propagating through the fluid at the inward flow portion and outward flow portion of a tube is provided. The measuring device provides at least one of an SOS signal indicative of the speed of sound propagating through the fluid, a GVF signal indicative of the gas volume fraction of the fluid and a reduced frequency indicative of the reduced frequency of the fluid. A processing unit determines a compensated mass flow rate measurement in response to at least one of the SOS signal, the GVF signal and the reduced frequency signal and the phase signal.

According to another embodiment of the present invention, a method for measuring the mass flow rate of an aerated fluid flowing in a pipe is provided. The method includes a vibrating pair of tubes having the fluid flowing therethrough. The tubes have an inward flow portion and an outward flow portion. The method includes measuring a phase signal indicative of a phase difference between a pair of tubes, and measuring the speed of sound propagating through the fluid at the inward flow portion and outward flow portion of a tube. The method further includes providing at least one of a SOS signal indicative of the speed of sound propagating through the fluid, a GVF signal indicative of the gas volume fraction of the fluid, and a reduced frequency indicative of the reduced frequency of the fluid. The method includes determining a compensated mass flow rate measurement in response to at least one of the SOS signal, the GVF signal and the reduced frequency signal and the phase signal.

The foregoing and other objects, features and advantages of the present invention will become more apparent in light of the following detailed description of exemplary embodiments thereof.

BRIEF DESCRIPTION OF THE DRAWINGS

FIG. 4 is a front view of a corilios meter.

FIG. 5 is a side elevational view of the coriolis meter of FIG. 4.

FIG. 6 is a cross sectional view taken along line A-A of the coriolis meter of FIG. 5.

FIG. 7 is a schematic illustration of model of a coriolis meter having fluid flowing therethrough, in accordance with the present invention.

BEST MODE FOR CARRYING OUT THE INVENTION

Coriolis meters provide a measurement of the mass flow and/or density of a fluid flow 12 passing through a pipe 14. As described in detail hereinbefore, a coriolis meter provides erroneous mass flow and density measurements in the presence of entrained gas within the fluid flow (e.g., bubbly gas). The present invention provides a means for compensating the coriolis meter to provide corrected or improved density and/or mass flow measurements.

Figure 1:
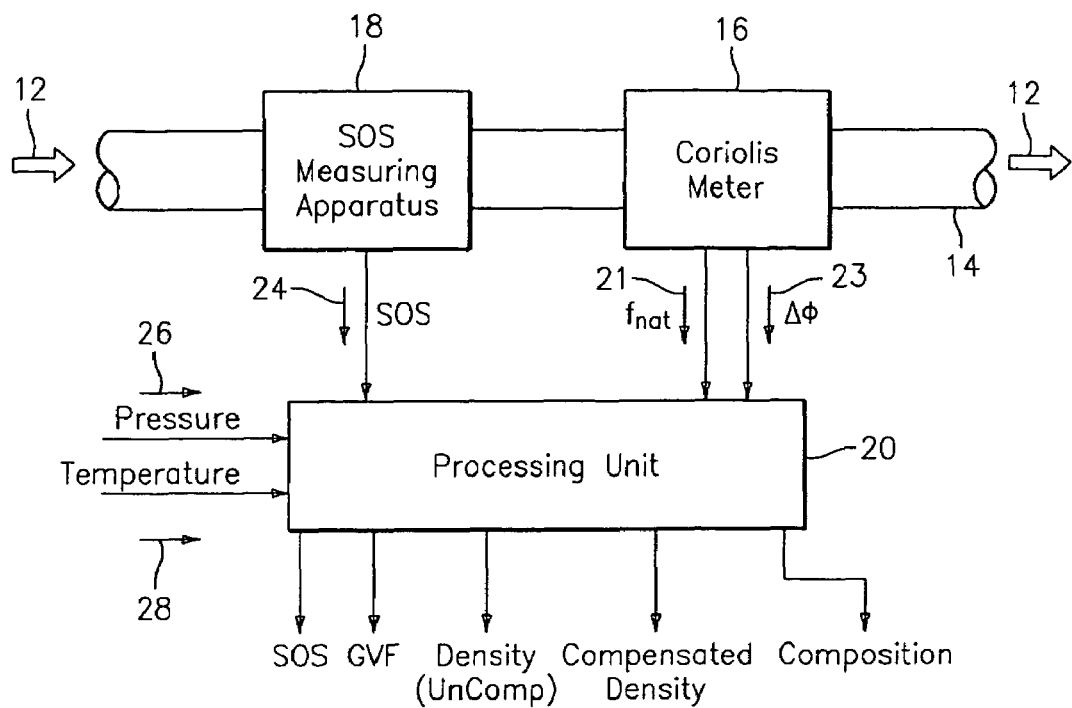
FIG. 1 is a schematic illustration of a flow measuring system for providing a density and/or mass flow rate measurement augmented for entrained gas within a fluid flow passing within a pipe, in accordance with the present invention.

As shown in FIG. 1, one embodiment of a flow measuring system 10 embodying the present invention includes a coriolis meter 16, a speed of sound (SOS) measuring apparatus 18 and a processing unit 20 to provide any one or more of the following parameters of the fluid flow, namely, gas volume fraction, speed of sound propagating through the fluid flow, uncompensated density, compensated density and composition. The fluid flow may be any aerated fluid or mixture including liquid, slurries, solid/liquid mixture, liquid/liquid mixture and any other multiphase flow.

In this embodiment, the coriolis meter 16 provides a frequency signal 22 indicative of the natural frequency of the fluid 12 loaded tubes of the coriolis meter and the phase signal 23 indicative of the phase lag in the tubes of the coriolis meter. The SOS measuring apparatus 18 provides an SOS signal 24 indicative of the speed of sound propagating through the fluid flow. A processing unit 24 processes the frequency signal, the phase signal and the SOS signal to provide at least one of the parameters of the fluid flow described hereinbefore. Pressure and/or temperature signals 26,28 may also be provided to the processing unit 20, which may be used to provide more accurate measurements of the gas volume fraction. The pressure and temperature may be measured by known means or estimated.

The coriolis meter may be any known coriolis meter, such as two inch bent tube coriolis meter manufactured my MicroMotion Inc. and a two in straight tube coriolic meter manufactured by Endress & Hauser Inc. The coriolis meters comprise a pair of bent tubes (e.g. U-shaped, pretzel shaped) or straight tubes as will be described hereinafter.

The SOS measuring device 18 includes any means for measuring the speed of sound propagating through the aerated flow 12. One method includes a pair of ultra-sonic sensors axially spaced along the pipe 14, wherein the time of flight of an ultrasonic signal propagating between an ultra-sonic transmitter and receiver. Depending on the characteristics of the flow, the frequency of the ultra-sonic signal must be relating low to reduce scatter within the flow. The meter is similar as that described in U.S. patent application Ser. No. 10/756,922 (CiDRA Docket No. CC-0699) filed on Jan. 13, 2004, which is incorporated herein by reference.

Figure 2:
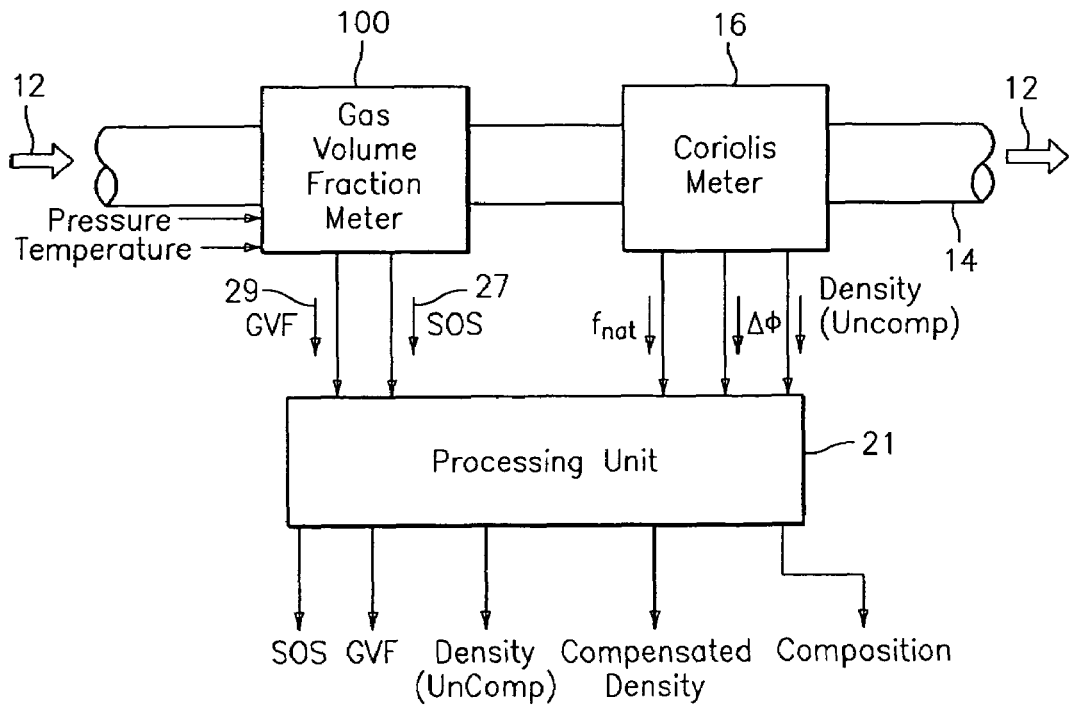
FIG. 2 is a schematic illustration of another flow measuring system for providing a density and/or mass flow rate measurement augmented for entrained gas within a fluid flow passing within a pipe, in accordance with the present invention.
Figure 23:
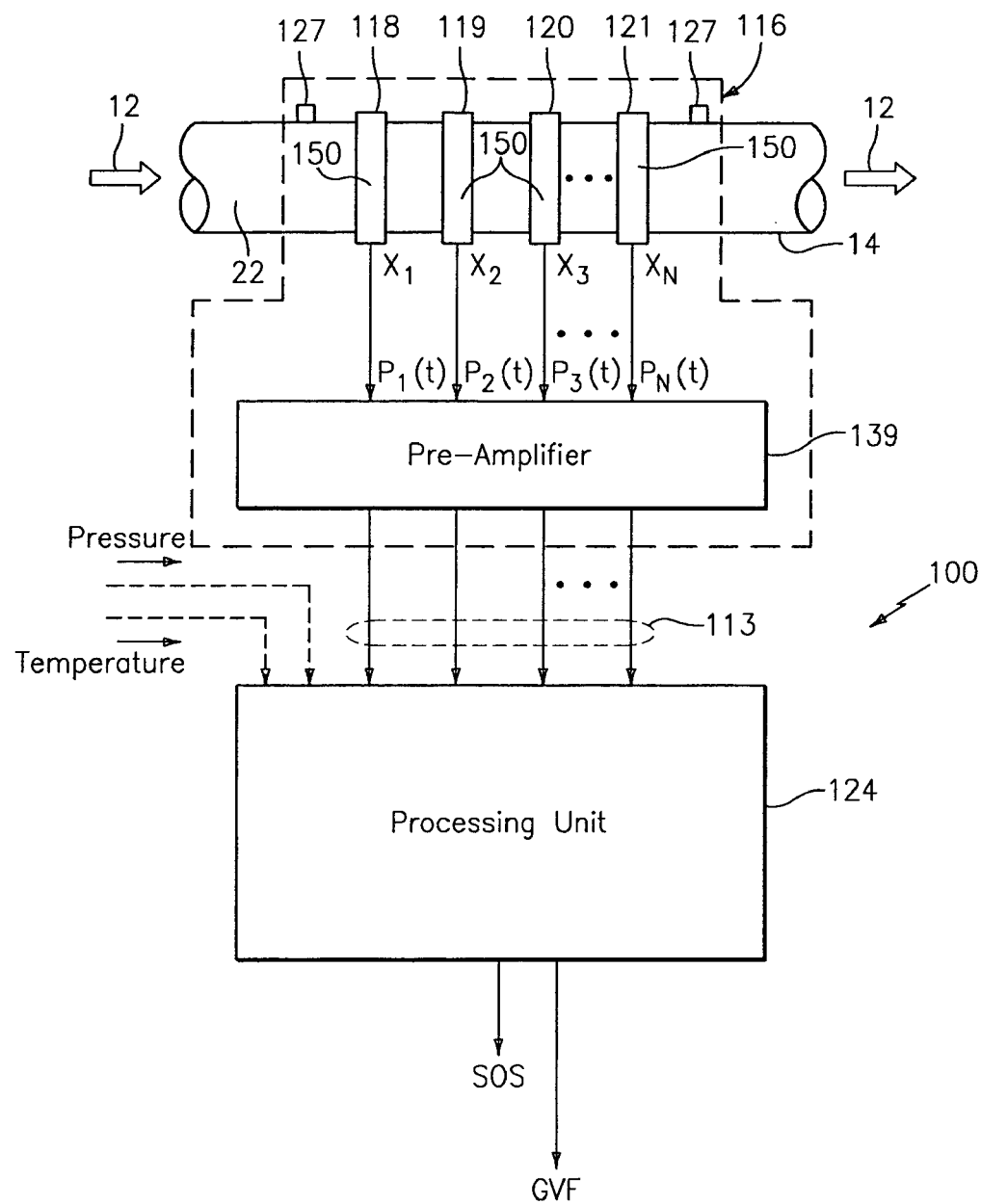
FIG. 23 is a schematic block diagram of a gas volume fraction meter, in accordance with the present invention.
Figure 24:
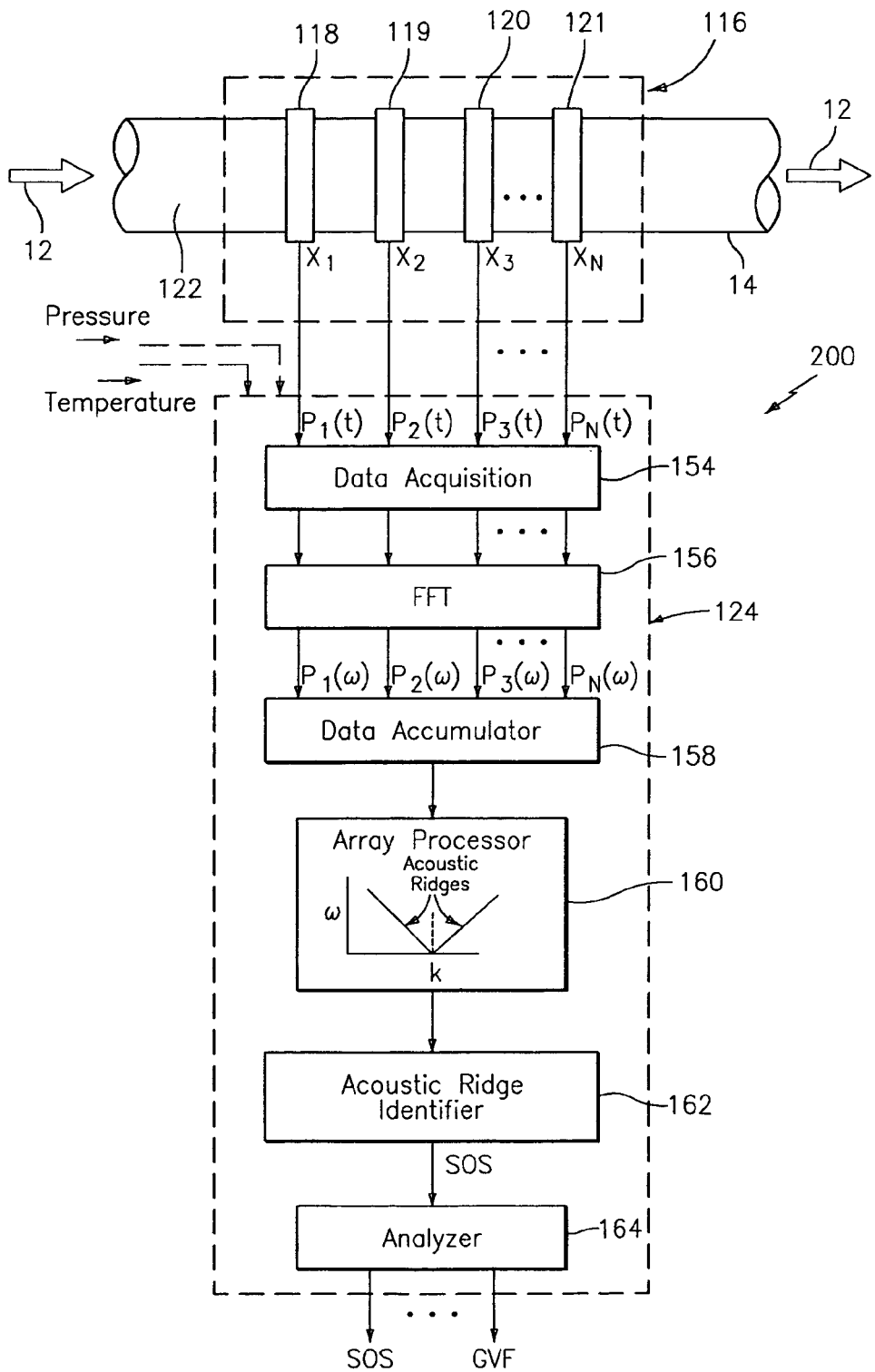
FIG. 24 is a schematic block diagram of another embodiment of gas volume fraction meter, in accordance with the present invention.

Alternatively, as shown in FIGS. 2, 23 and 24, the SOS measuring apparatus may be a gas volume fraction (GVF) meter that comprises a sensing device 116 having a plurality of strain-based or pressure sensors 118-121 spaced axially along the pipe for measuring the acoustic pressures 190 propagating through the flow 12. The GVF meter 100 determines and provides a first signal 27 indicative of the SOS in the fluid and a second signal 29 indicative of the gas volume fraction (GVF) of the flow 12, which will be described in greater detail hereinafter.

Figure 3:
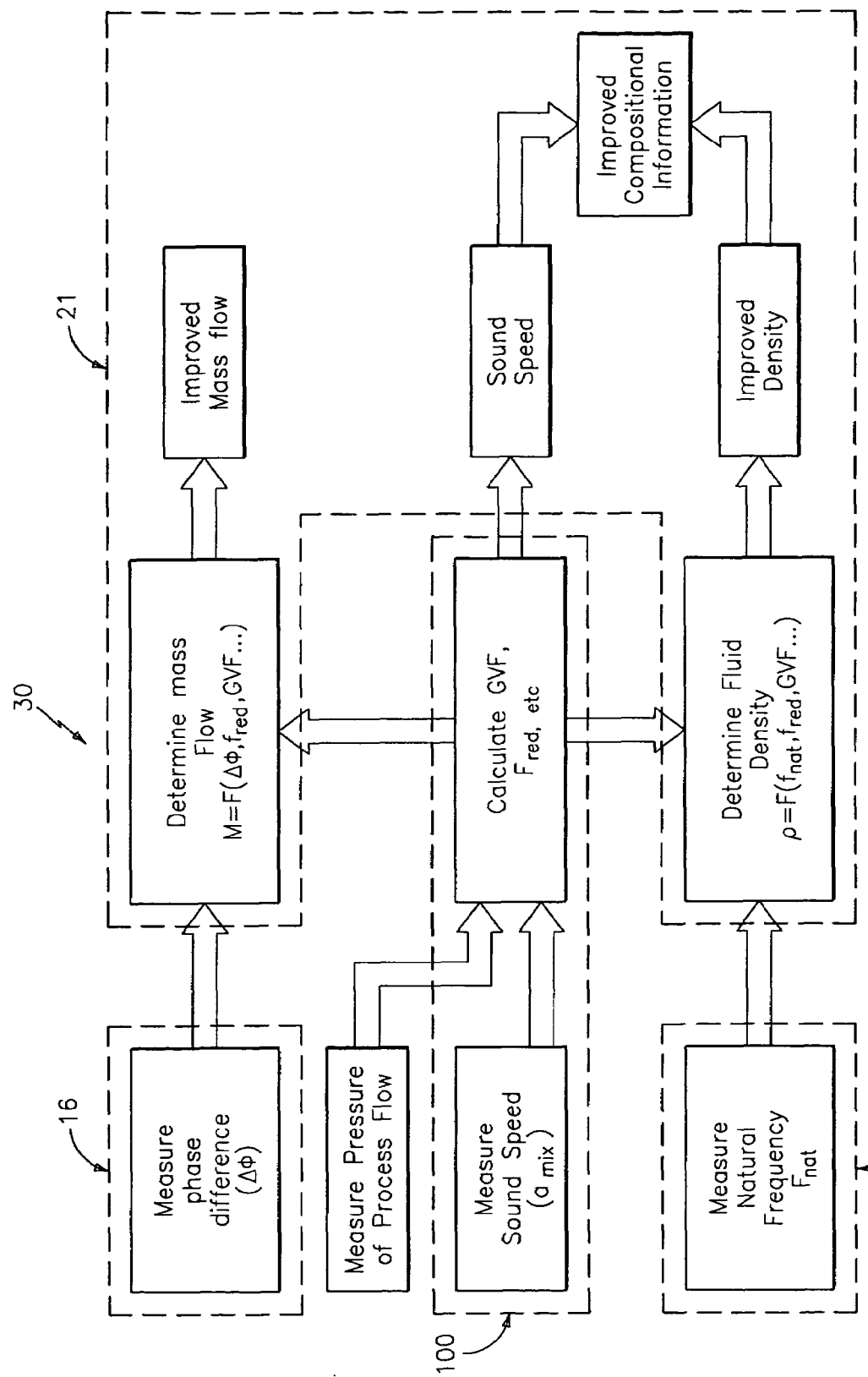
FIG. 3 is a function block diagram of a processing unit of flow measuring system similar to that of FIG. 1, in accordance with the present invention.

FIG. 3 illustrates a functional block diagram 30 of the flow measuring system of FIG. 2. As shown, the GVF meter 100 measures acoustic pressures propagating through the fluids to measure the speed of sound $\alpha_{mix}$. The GVF meter calculates at least gas volume fraction of the fluid and/or the reduced natural frequency using the measured speed of sound. The GVF meter may also use the pressure of the process flow to determine the gas volume fraction. The pressure may be measured or estimated.

For determining an improved density for the coriolis meter, the calculated gas volume fraction and/or reduced frequency is provided to the processing unit 21. The improved density is determined using analytically derived or empirically derived density calibration models (or formulas derived therefore), which is a function of the measured natural frequency and at least one of the determined GVF, reduced frequency and speed of sound, or any combination thereof, which will be described in greater detail hereinafter. The improved density measurement is the density of the aerated flow passing through the pipe.

The present invention further contemplates determining improved compositional information of the aerated flow. In other words, knowing the speed of sound propagating through the flow and the improved density, the processing unit 21 can determine density of the fluid/mixture portion of the multiphase flow.

For example, the density ($\rho_{mix}$) of an aerated flow is related to the volumetric phase fraction of the components ($\varnothing_i$) and the density of the components ($\rho_i$).

$$\rho_{mix} = \sum_{i=1}^{N} \phi_i \rho_i$$

Where continuity requires:

$$\sum_{i=1}^{N} \phi_i = 1$$

The system 10 provides an improved measure of the density of the aerated flow. For a two-component mixture, knowing the density ($\rho_{gas}$), gas volume fraction (or SOS) and accurately measuring the mixture density ($\rho_{mix}$) provides a means to determine the density ($\rho_{nongas}$) of the non-gas portion of the fluid flow. For example, for a two-component fluid flow:

$$\rho_{mix} = \rho_{nongas}\phi_{nongas} + \rho_{gas}\phi_{gas}$$

therefore, $\rho_{nongas} = (\rho_{mix} - \rho_{gas}\phi_{gas})/\phi_{nongas}$, wherein $\phi_{nongas} = 1 - \phi_{gas}$ wherein $\rho_{mix}$ is the density of the mixture, $\rho_{nongas}$, $\varnothing_{nongas}$ are the density and phase fraction, respectively, of a non-gas component of the fluid flow, and $\rho_{gas}$, $\varnothing_{gas}$ are the density and phase fraction, respectively, of the entrained gas within the mixture.

Therefore, knowing the density ($\rho_{gas}$) of the gas/air, the measured gas volume fraction of the gas ($\varnothing_{gas}$), and the improved density measurement ($\rho_{mix}$) of the aerated flow to be compensated for entrained gas enable the density ($\rho_{nongas}$) of the non-gas portion of the aerated flow 12 to be determined, which provides improved compositional information of the aerated flow 12.

The present invention also contemplates compensating or improving the mass flow rate measurement of the coriolis meter 16, as shown in FIG. 3. For determining an improved mass flow rate for the coriolis meter, the calculated gas volume fraction and/or reduced frequency is provided to the processing unit 21. The improved mass flow rate is determined using analytically derived or empirically derived mass flow calibration models (or formulas derived therefore), which is a function of the measured phase difference ($\Delta\phi$) and at least one of the determined GVF, reduced frequency and speed of sound, or any combination thereof, which will be described in greater detail hereinafter. For determining an improved density for the coriolis meter, the calculated gas volume fraction and/or reduced frequency is provided to the processing unit 21. The improved density is determined using analytically derived or empirically derived density calibration/parameter models (or formulas derived therefore), which is a function of the measured natural frequency and at least one of the determined GVF, reduced frequency and speed of sound, or any combination thereof, which will be described in greater detail hereinafter. The improved mass flow measurement is the mass flow rate of the aerated flow passing through the pipe.

While the improved mass flow and improved density measurement may be a function GVF, SOS and reduced frequency, the present invention contemplates these improved measurements may be a function of other parameters, such a gas damping $\zeta_{gas}$.

Further, while the functional block diagram illustrates that the processing unit 21 may improve both the density measurement and the mass flow measurement of the coriolis meter 16, the invention contemplates that the processing may only compensate or improve one of the density and mass flow rate parameters.

Referring to FIG. 7, a lumped-parameter aeroelastic model provides a first-principles basis to analyze the effects of aeration on coriolis based mass and density measurements. As shown, the model can be used to illustrate qualitatively the role of several non-dimensional parameters which govern the performance of the coriolis meters. It can be concluded from these models that gas volume fraction plays a dominant role, with several other parameters including gas damping $\zeta_{gas}$ and reduced frequency also influencing performance.

Although simplified models may provide some insight into the influence of various parameters, quantitative models remain elusive due to the inherent complexity of multiphase, unsteady fluid dynamics. Attempts to mitigate the effects of aeration on coriolis measurements have proven to be a challenging endeavor. Firstly, introducing aeration transforms the coriolis meter from a well-understood device operating in quasi-steady parameter space into a device operating in a complex, non-homogeneous, multiphase parameter space. The impact of the complexity is further magnified by the inability of current coriolis meters to accurately determine the relevant aeroelastic operating parameters, namely the inability to precisely determine the gas volume fraction nor the reduced frequency of operation.

The present invention presents an approach in which a speed-of-sound measurement of the process fluid is integrated with a coriolis meter to form a system with an enhanced ability to operate accurately on aerated fluids. A schematic of a speed-of-sound augmented coriolis system is shown in FIG. 3. Introducing a real time, speed-of-sound measurement address the effects of aeration on multiple levels with the intent to enable coriolis meters to maintain mass flow and liquid density measurements in the presence of entrained air with accuracy approaching that for non-aerated liquids. Firstly, by measuring the process sound speed with process pressure, the aeration level of the process fluid can be determined with high accuracy on a real time basis. Secondly, the real time measurements of sound speed and the derived measurement of gas volume fraction are then utilized with analytically or empirically derived correction factors to improve the interpretation of the measured phase difference and natural frequency of the vibrating tubes in terms of the density of the aerated fluid.

The lumped parameter aeroelastic model for coriolis meters operating in aerated fluids incorporates the effects of compressibility and inhomogeneity association with entrained gases. The model identifies several aeroelastic parameters that influence the relationship between quantities directly measured by the coriolis meter and the interpreted fluid mass flow and density.

The effect of aeration was evaluated using the model for a set of representative coriolis meters spanning a range of tube natural frequencies. Results of the model show that the low frequency coriolis meter analyzed was significantly less sensitivity to errors associated with the aeroelastic effects of aeration than the higher frequency designs.

A system 10 is provided to enhance the performance of coriolis meters on aerated fluids. The system utilizes a speed-of-sound measurement of the process fluid integrated with a coriolis meter. Measuring fluid sound speed enables the determination of real-time aeroelastic operating parameters which enables the meter to accurately interpret the directly measured phase difference and natural frequency of the tubes in terms of fluid mass flow and density in the presence of aeration.

The aeroelastic model addresses U-tube coriolis meters containing radially outward and inward flows of an aerated fluid. The mass flow rate and density of the fluid measured by the coriolis meter is given by a solution of an eigenvalue problem governing the dynamics of the aeroelastic system. Mass flow is determined by the phase lag between the displacement of the out-bound and in-bound tubes in the lowest-frequency bending mode of the system. Fluid density is related to the natural frequency of this mode.

The aerated fluid is assumed to be a well-mixed, dispersed bubbly flow in which the bubbles are small compared to the diameter of the tube. Under this assumption, the effects of compressibility can be incorporated using a lumped parameter model of the first acoustic cross mode of the tube. The effects of inhomogeneity introduced by the bubbles are incorporated using a lumped parameter model of a bubble in a oscillatory acceleration field contained in an viscous, incompressible fluid. The resulting aeroelastic equations of motion for the coriolis meter show the behavior of the system is influenced by non-dimensional parameters characterizing the aerated mixtures including reduced frequency, void fraction, and fluid viscosity parameters.

The model is exercised to examine the effect of aeration for a range of parameters considered to be broadly representative of the commercially available coriolis meters. Results show that aeration can significantly influence the aeroelastic behavior of coriolis meters, but that, if appropriately considered, coriolis meters can be used to provide accurate characterization of aerated fluids.

Although the specific design parameters of coriolis meters are many and varied, all coriolis meters are essentially aeroelastic devices. Aeroelasticity is a term developed in the aeronautical sciences that describes the study of dynamic interaction of coupled fluid dynamic and structural dynamic systems, for example the static and dynamic response of an aircraft under aerodynamic forces. Coriolis flow meters rely on characterizing the aeroelastic response of fluid-filled, vibrating flow tubes to determine both the mass flow rate and process fluid density measurements.

Quasi-Steady Model

Most coriolis meters rely on quasi-steady models of the interaction between the structural and fluid dynamics within the meter to determine both mass flow and density. In a quasi steady model, the fluid within the flow tubes is assumed to be incompressible and homogenous. The fluid essentially adds inertial terms associated with translation, centrifuigal and coriolis acceleration to the vibrational dynamics of the flow tubes.

FIGS. 4 and 5 show a schematic of a generic U-tube coriolis meter. The coriolis meter consists of two U-shaped flow tubes vibrating primarily in an out-of-plane bending mode. The dynamics of the typical section, shown as section A-A in FIGS. 5 and 6 are considered to develop a lumped-parameter, aeroelastic model of the coriolis meter. FIG. 7 provides a schematic of a lump-parameter, quasi-steady model for the typical section dynamics.

The aeroelastic model assumes symmetry about the centerline. The bending stiffness and inertia of each tube is modeled independently, with the tubes coupled structurally using a torsional spring to represent the torsional stiffness of the U-tube. The translational inertia of the fluid adds linearly to the inertia associated with the tubes. The out-of-plane vibration of the fluid flowing within the tubes generates a coriolis force that acts to damp the vibration of the tube with the radially outward flow, and feeds the vibration in the radially inward flow tube.

The equations of motion for the quasi-steady model depicted in FIG. 7 are given below. First term represents the translation mass of the fluid and the structure, the second represents the Coriolis force acting on the fluid with radially velocity U at a radial position R. The last two terms represent the spring forces from the structural and torsion springs depicted in the schematic.

$$(M_{struct} + M_{fluid})\frac{d^2 x_1}{dt^2} + 2M_{fluid}\frac{U}{R}\frac{dx_1}{dt} + K_{struct}x_1 + \frac{K_{torsion}}{L}(x_1 - x_2) = 0$$

$$(M_{struct} + M_{fluid})\frac{d^2 x_2}{dt^2} - 2M_{fluid}\frac{U}{R}\frac{dx_2}{dt} + K_{struct}x_2 + \frac{K_{torsion}}{L}(x_2 - x_1) = 0$$

The equations of motion of the above lumped parameter model, assuming solutions in the form of $e^{ST}$ where s is the complex frequency, can be expressed in non-dimensional form as:

$$\begin{bmatrix} -\frac{2\alpha}{1+\alpha}U_{nd} - s & -\frac{1+\Gamma}{1+\alpha} & 0 & \frac{\Gamma}{1+\alpha} \\ 1 & -s & 0 & 0 \\ 0 & \frac{\Gamma}{1+\alpha} & \frac{2\alpha}{1+\alpha}U_{nd} - s & -\frac{1+\Gamma}{1+\alpha} \\ 0 & 0 & 1 & -s \end{bmatrix} \begin{Bmatrix} y_1 \\ x_1 \\ y_2 \\ x_2 \end{Bmatrix} = 0$$

The parameters governing the dynamic response of the model are defined in Table 1.

TABLE 1

Definition of Non-dimensional Parameters Governing the Equation of Motion for the Lumped Parameter Quasi-Steady Coriolis Meter

| Symbol | Description | Definition |
|---|---|---|
| α | Mass ratio | $m_{fluid}/m_{struct}$ |
| Γ | Torsinal Spring Parameter | $K_{torsion}/K_{struct}L$ |
| $U_{nd}$ | Radial Flow Velocity | $U/\omega_{struct}R$ |
| τ | Non-dimensional time | $t\,\omega_{struct}$ |
| y | Non-dimensional temporal derivative of x | $dx/d\tau$ |

Solving the fourth-order eigenvalue problem described provides a means to analytically link the fluid input parameters to the dynamic response of the coriolis meter. Specifically, the radial flow velocity parameter, $U_{nd}$, is closely related to fluid mass flow and influence the phase lag between the tubes in the first bending mode. α, the fluid mass parameter, directly influences the natural frequency of the first bending mode.

Figure 8:
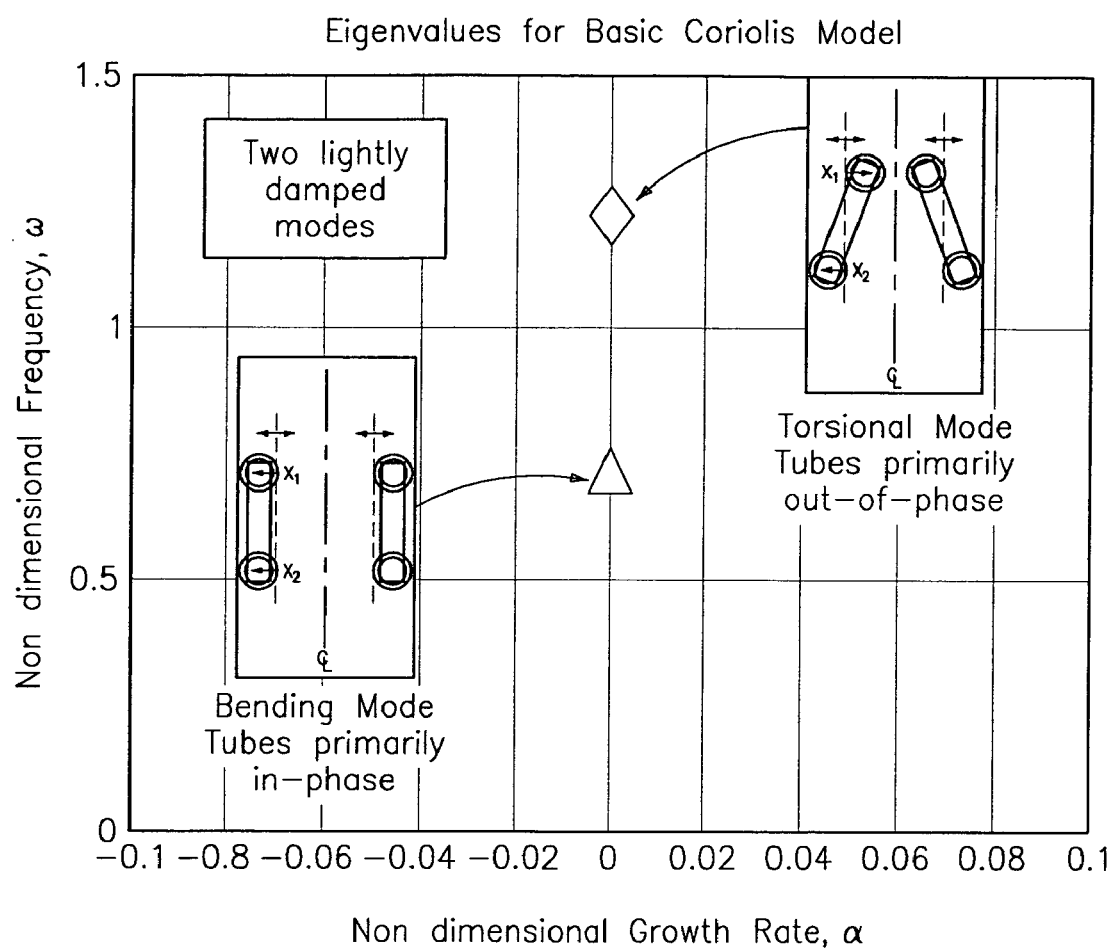
FIG. 8 is a plot of the eigenvalues for a basic coriolis model in accordance with the present invention.

FIG. 8 shows the eigenvalues for the quasi-steady model for a coriolis meter with the parameters given in Table 2. The dimensional parameters for the representative coriolis meter are given in Table 3. As shown, the quasi-steady model has two, lightly damped modes of oscillation. The location of the eigenvalues do not change significantly with mass flow. The lower frequency mode is primarily associated with bending, and the higher frequency mode in which the tubes are predominately out-of-phase torsional mode.

TABLE 2

Definition of Non-dimensional Parameters Governing the Equation of Motion for the Lumped Parameter QuasiSteady Coriolis Meter

| Symbol | Description | Value |
|---|---|---|
| α | Mass ratio | 1.0 |
| Γ | Torsional Spring Parameter | 1.0 |
| $U_{nd}$ | Radial Flow Velocity | 0-.015 |

TABLE 3

Dimensional Parameters Defining the Baseline Vibrating Tube Density Meter

| Parameter | Description | Value |
|---|---|---|
| $f_s$ | Structural Frequency of Tubes | 100 Hz |
| D | Tube diameter | 2.0 inches |
| R | Radial Position of Typical Section | 20 inches |
| t | Wall thickness | 0.060 inches |
| $\rho_{fluid}$ | Liquid Density | 1000 kg/m^3 |
| $\rho_{struct}$ | Tube Density | 8000 kg/m^3 |
| mdot | Mass flow | 0-10 kg/sec |
| U | Fluid Velocity | 0-5 m/sec |

Figure 9:
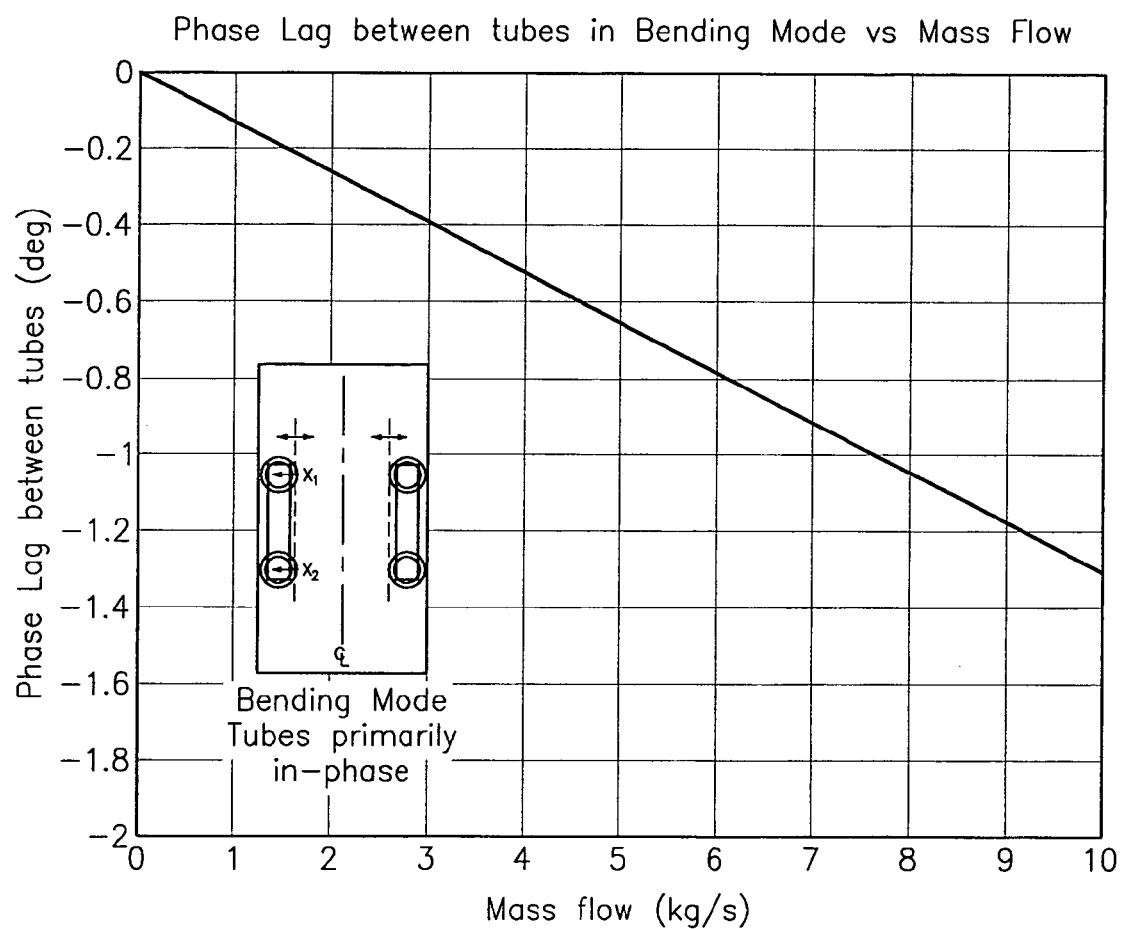
FIG. 9 is a plot of the phase lag between the tubes of a coriolis meter as a function of the mass flow rate in accordance with the present invention.

Most commercial coriolis meters leverage the information contained in the lower frequency bending mode to determine the mass flow rate and density of the fluid, namely the phase lag between the outbound and inbound tubes and the frequency of oscillation, respectively. FIG. 9 shows the phase lag between the two tubes as a function of mass flow. As shown, the phase lag scales directly with the mass flow through the coriolis meter. The change in phase with mass flow rate is, however, relatively small, changing approximately 1 degree for a 10 kg/sec change in mass flow this coriolis meter.

Figure 10:
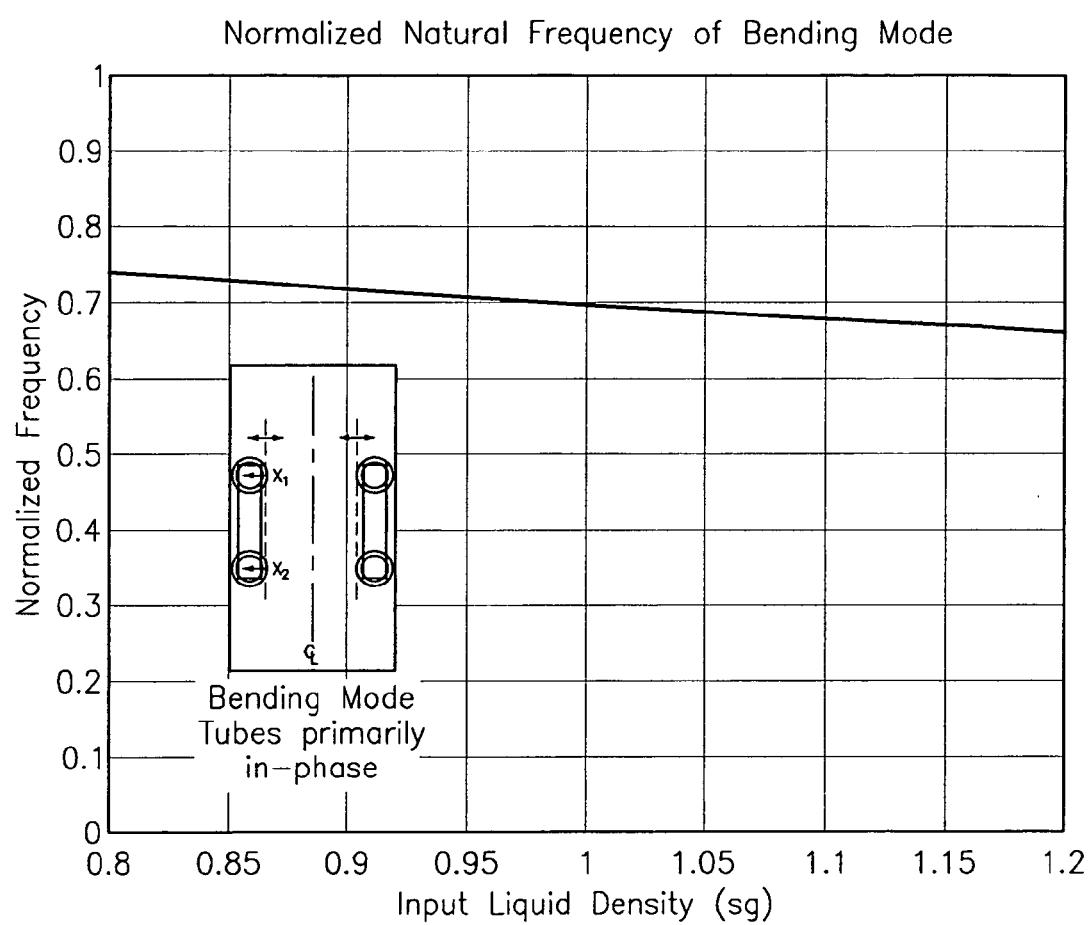
FIG. 10 is a plot of the normalized natural frequency of the bending mode as a function of the input liquid density in accordance with the present invention.

The normalized natural frequency of the primarily bending mode is shown as a function liquid density in FIG. 10. For this coriolis meter with an structural frequency of 100 hz operating on water, a 10% change is density corresponds to approximately 2 Hz change in resonant frequency.

The aeroelastic model developed above illustrates the basic operating principles of coriolis meters operating based on a quasi-steady model of the interaction between the fluid and the structure. The accuracy of the fluid measurements made by coriolis meter operating under this assumption is directly impacted by the validity of this assumption. In this section, an aeroelastic model for a coriolis meter is developed in which the quasi-steady assumption is relaxed, and the effects of fluid compressibility and inhomogeneity, typically associated with aerated liquids, are introduced.

Fluid Compressibility

It is well known that most aerated liquids are significantly more compressible than non-aerated liquids. Compressibility of a fluid is directly related to the speed of sound and density of the fluid. Mixture density and sound speed can be related to component densities and sound speed through the following mixing rules which are applicable to single phase and well-dispersed mixtures and form the basis for speed-of-sound-based entrained air measurement.

$$\kappa_{mix} = \frac{1}{\rho_{mix} a_{mix_\infty}^2} = \sum_{i=1}^{N} \frac{\phi_i}{\rho_i a_i^2}$$

where $$\rho_{mix} = \sum_{i=1}^{N} \rho_i \phi_i$$

and $\kappa_{mix}$ is the mixture compressibility, and $\phi_i$ is the component volumetric phase fraction.

Consistent with the above relations, introducing gases into liquids dramatically increased the compressibility of the mixture. For instance, at ambient pressure, air is approximately 25,000 times more compressible than water. Thus, adding 1% entrained air increases the compressibility of the mixture by a factor of 250. Conceptually, this increase in compressibility introduces dynamic effects that cause the dynamic of behavior of the aerated mixture within the oscillating tube to differ from that of the essentially incompressible single-phase fluid.

Figure 11:
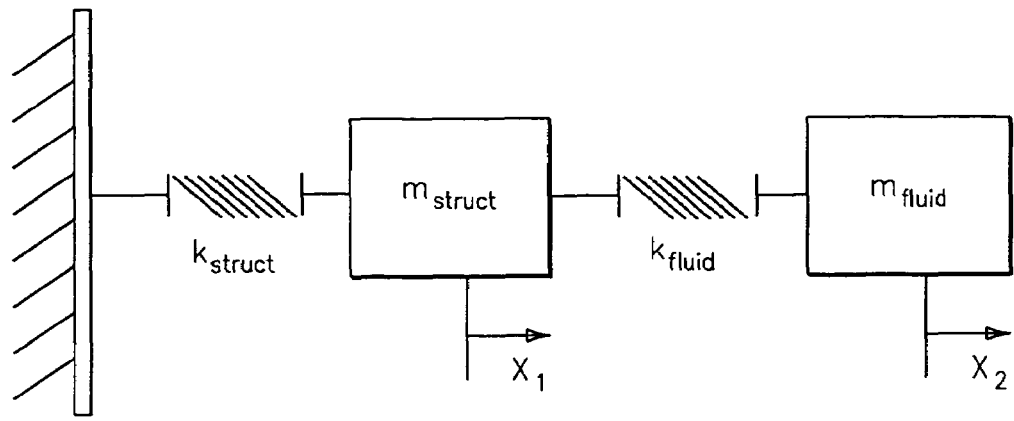
FIG. 11 is a schematic illustration of model of a coriolis meter having aerated fluid flowing therethrough that accounts for compressibility of the aerated fluid, in accordance with the present invention.

The effect of compressibility of the fluid can be incorporated into a lumped parameter model of a vibrating tube as shown schematically in FIG. 11. The stiffness of the spring represents the compressibility of the fluid. As the compressibility approaches zero, the spring stiffness approaches infinity and the model becomes equivalent one in which the mass of the fluid is directly lumped onto the mass of the structure as the model presented in FIG. 7.

The natural frequency of the first transverse acoustic mode in a circular duct can be used to estimate an appropriate spring constant for the model $$f = \frac{1.84}{\pi D} a_{mix} = \frac{1}{2\pi} \sqrt{\frac{K_{fluid}}{m_{fluid}}}$$

Note that this frequency corresponds to a wavelength of an acoustic oscillation of approximately two diameters, i.e., this transverse mode is closely related to a "half wavelength" acoustic resonance of the tube.

Figure 12:
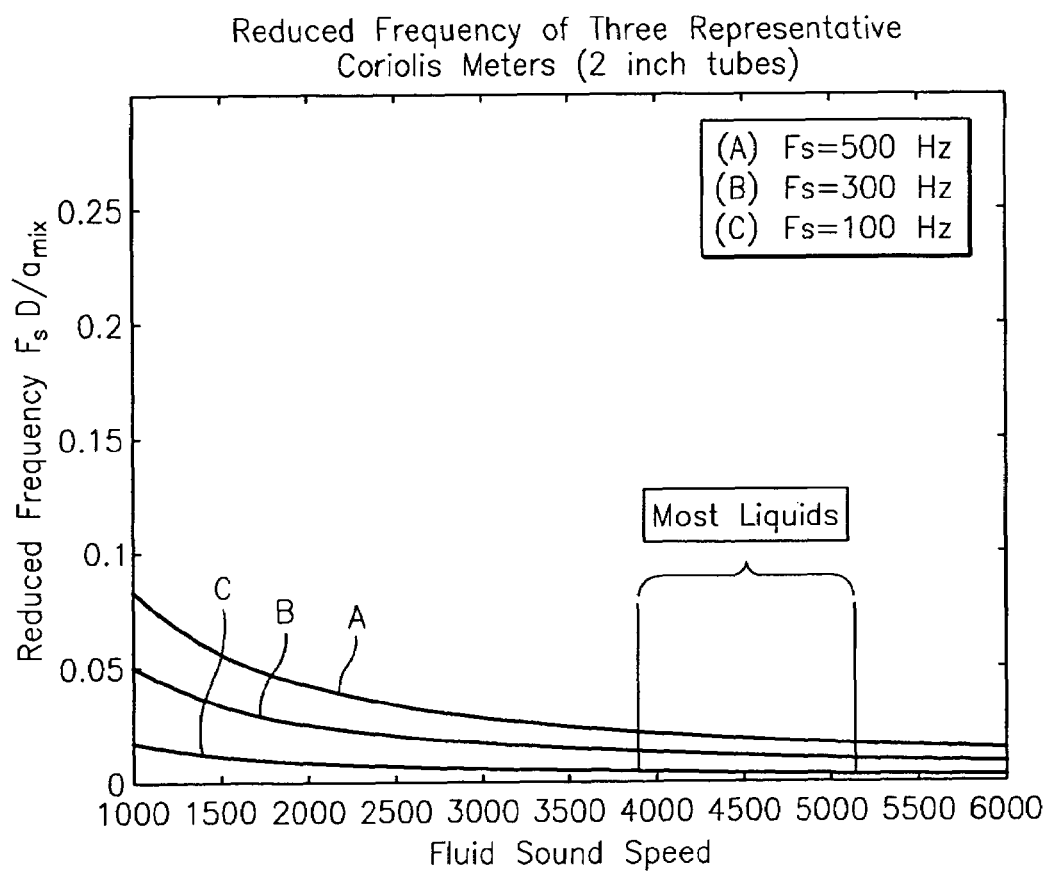
FIG. 12 is a plot of the reduced frequency of three representative coriolis meters as a function of fluid sound speed in accordance with the present invention.

In characterizing aeroelastic systems, it is often convenient to define a reduced frequency parameter to gauge the significance of the interaction between coupled dynamic systems. For a vibrating tube filled with fluid, a useful reduced frequency can be defined as a ratio of the natural frequency of the structural system to that of the fluid dynamic system.

$$f_{red} = \frac{f_{struct} D}{a_{mix}}$$

Where $f_{struct}$ is the natural frequency of the tubes in vacuum, D is the diameter of the tubes, and $a_{mix}$ is the sound speed of the process fluid. Strictly speaking, quasi-steady models are valid for systems in which the reduced frequency is small, i.e. negligible compared to unity. In these cases, models which neglect the compressibility of the fluid are likely to be sufficient. However, the effects of unsteadiness increase with increasing reduced frequency. FIG. 12 shows the reduced frequency as a function of fluid sound speed for three representative coriolis meters.

Figure 13:
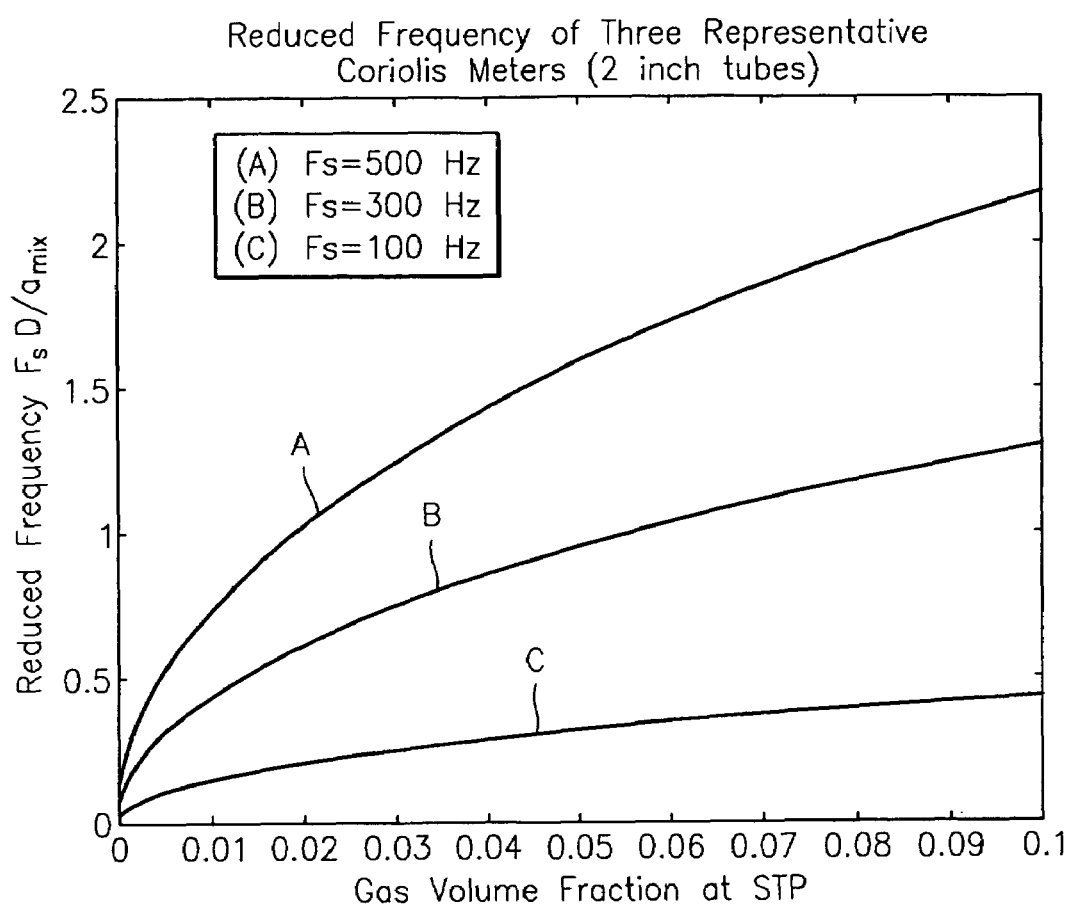
FIG. 13 is a plot of the reduced frequency of three representative coriolis meters as a function of gas volume fraction at stand temperature and pressure in accordance with the present invention.

For a given coriolis meter, mixture sound speed can have a dominant influence of changes in reduced frequency. FIG. 13 shows the reduced frequency plotted as a function of gas volume fraction of air in water at standard temperature and pressure for a 2-inch diameter tubes with a structural natural frequencies ranging from 100 Hz to 500 Hz. As shown, the reduced frequency is quite small for the non-aerated water. However, it builds rapidly with increasing gas volume fraction, indicating that the significance of compressibility increases with gas volume fraction. Small levels of gas volume fraction can result in significant reduced frequencies, with the impact of gas increasing in severity with tube natural frequency, and similarly, increases with tube diameter.

Fluid Inhomogeneity

In additional to dramatically increasing the compressibility of the fluid, aeration also introduces inhomogeneity to the mixture. For flow regimes in which the gas is entrained in a liquid-continuous flow field, the first-order effects of the aeration can be modeled using bubble theory. By considering the motion of an incompressible sphere of density of $\rho_0$ contained in an inviscid, incompressible fluid with a density of $\rho$ and set into to motion by the fluid, Landau and Lipshitz, show that the velocity of the sphere is given by:

$$V_{sphere} = \frac{3\rho}{\rho + 2\rho_0} V_{fluid}$$

For most entrained gases in liquids, the density of the sphere is orders of magnitude below that of the liquid, and the velocity of bubble approaches three times that of the fluid in inviscid mixture.

Considering this result in the context of the motion of a sphere in a cross section of a vibrating tube, the increased motion of the sphere compared to the remaining fluid must result in a portion of the remaining fluid having a reduced level of participation in oscillation, resulting in a reduced, apparent system inertia.

Figure 15:
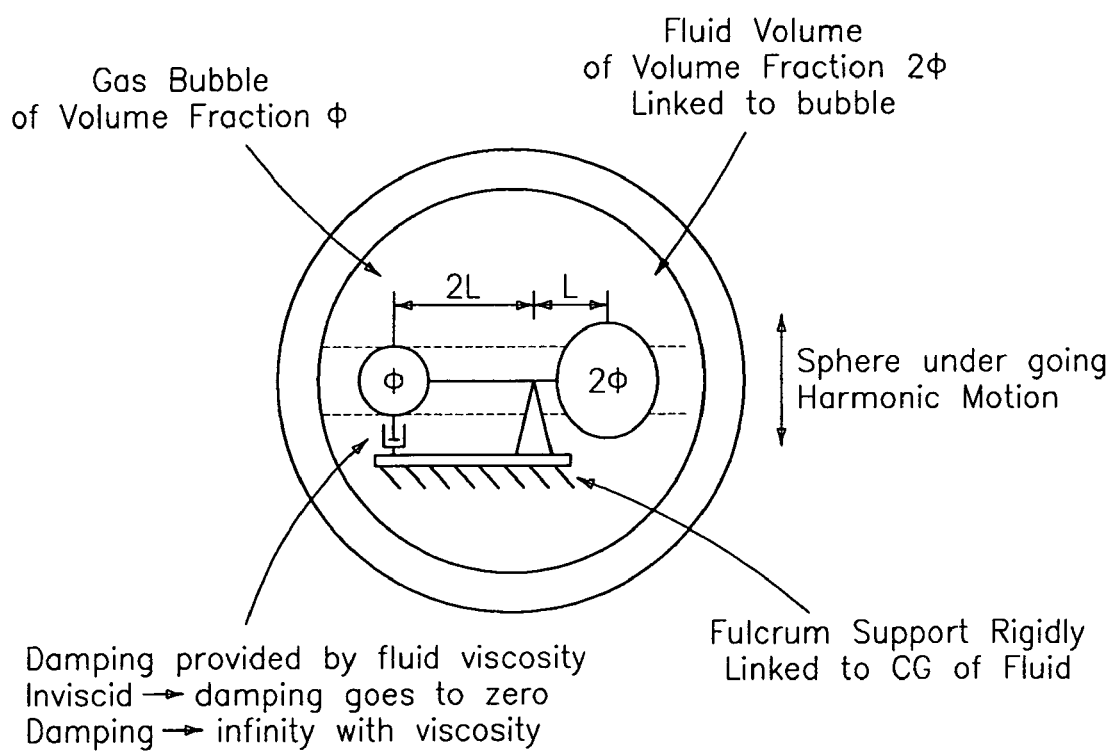
FIG. 15 is a schematic diagram of effect of fluid flow inhomogeneity with the tube of a coriolis meter, in accordance with the present invention.

FIG. 15 illustrates a lumped parameter model for the effects of inhomogeniety in the oscillation of an aerated-liquid-filled tube. In this model, a gas bubble of volume fraction $\phi$ is connected across a fulcrum to a compensating mass of fluid with volume $2\phi$. The fulcrum attached to center of mass of the fluid of the remaining fluid within the tube. The effect of viscosity is modeled using a damper connected to restrict the motion of the gas bubble with respect to the rest of the liquid. The remaining volume of liquid in the tube cross section ($1-3\phi$) is filled with an inviscid fluid.

Figure 14:
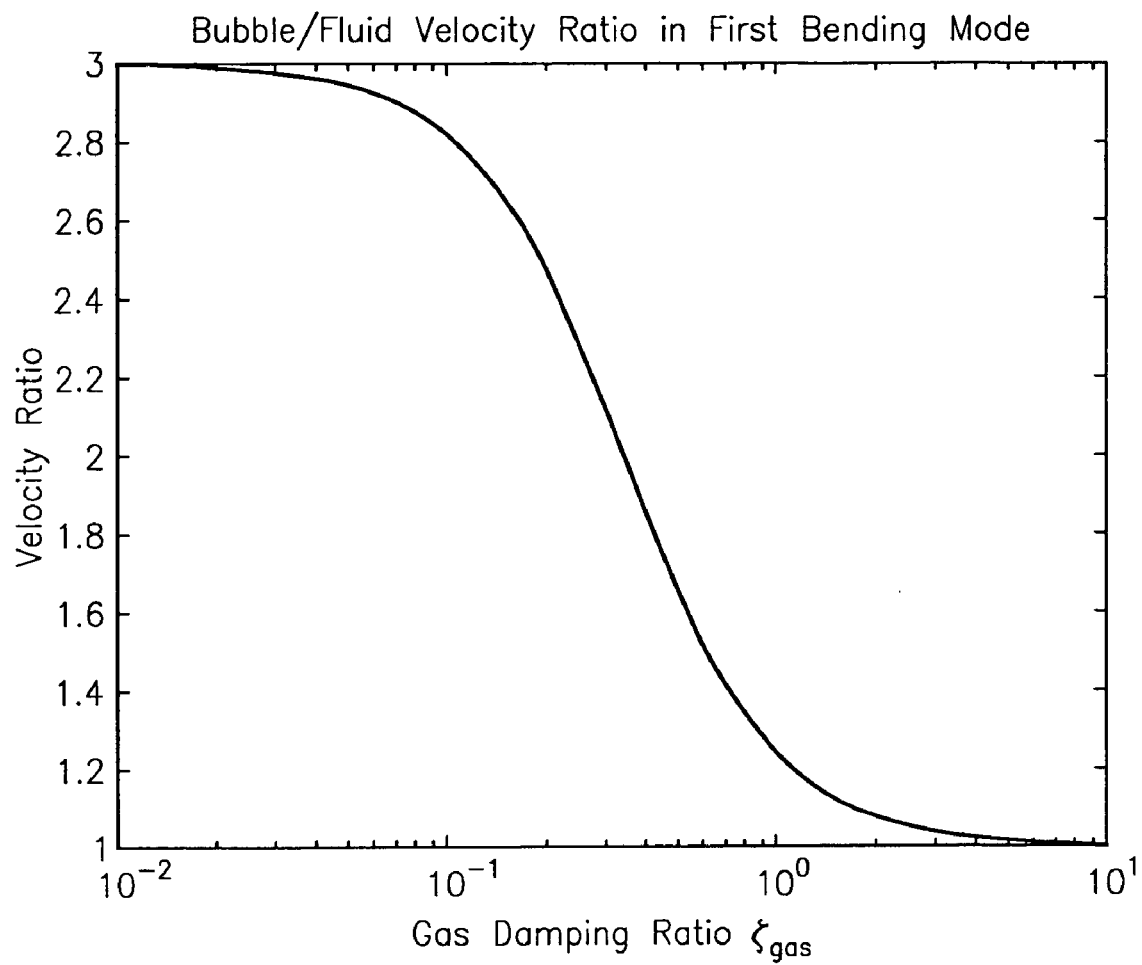
FIG. 14 is a plot of the bubble/fluid velocity ratio in the first bending mode as a function of the gas damping ratio in accordance with the present invention.

In the inviscid limit, the compensating mass of fluid ($2\phi$) does not participate in the oscillation of remaining fluid, and the velocity of the mass-less gas bubble approaches three times the velocity of the remaining fluid. The velocity ratio between the bubble and the remaining fluid is shown in FIG. 14 as a function of gas damping ratio defined in Table 4. The effect of this relative motion is to reduce the effective inertia of the fluid inside the tube to ($1-3\phi$) times that presented by a homogeneous fluid-filled the tube. In the limit of high viscosity, the increased damping constant minimizes the relative motion between the gas bubble and the liquid, and the effective inertia of the aerated fluid approaches $1-\phi$.

The effective inertia an aerated, but incompressible, fluid oscillating within a tube predicted by this model is consistent with known potential theory models in the limits of high and low viscosities.

TABLE 4

Definition of Non-dimensional Parameters Governing the Equation of Motion for the Aeroelastic, Lumped Parameter Model of a Coriolis Meter with a Compressible, Aerated Fluid

| Symbol | Description | Definition |
|---|---|---|
| $\phi$ | Gas Volume Fraction | |
| $Q$ | Natural Frequency Ratio | $\omega_{fluid}/\omega_{struct}$ |
| $\zeta_f$ | Critical Damping Ratio of Fluid System | $b_{fluid}/(2m_{fluid}\omega_{fluid})$ |
| $\zeta_s$ | Critical Damping Ratio of Structural System | $b_{struc}/(2m_{struct}\omega_{sstruc})$ |
| $\zeta_g$ | Critical Damping Ratio of Structural System | $b_{gas}/(2(2\phi)m_{fluid}\omega_{struct})$ |

Combined Lumped Parameter Model

Figure 16:
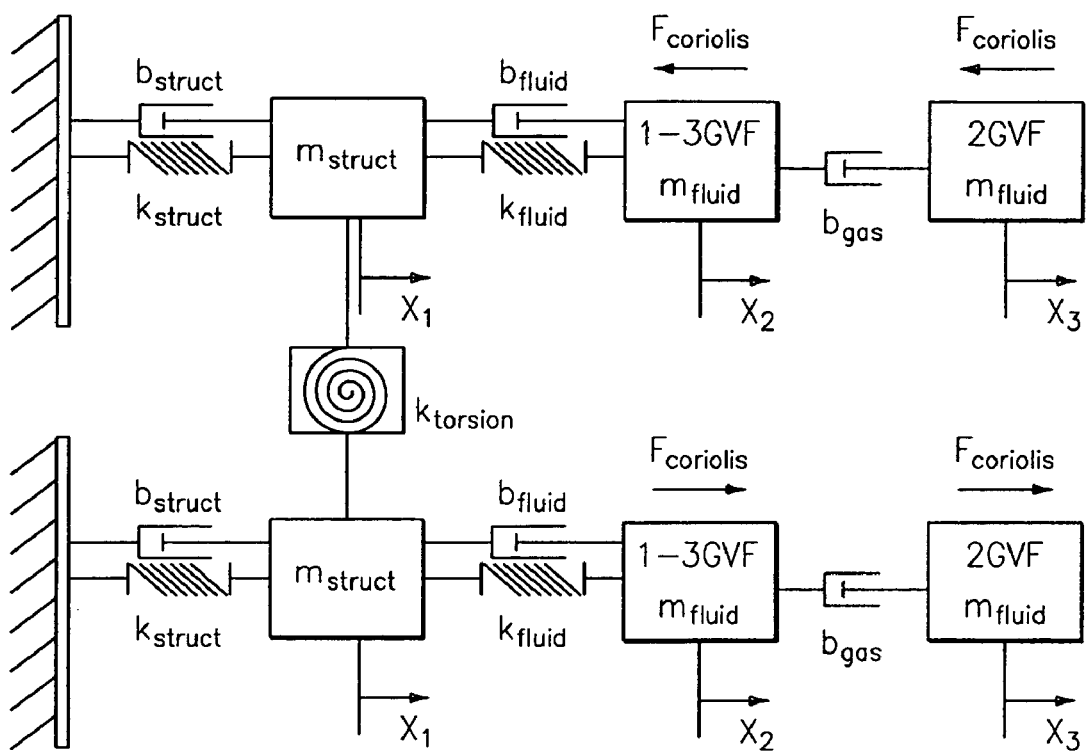
FIG. 16 is a schematic illustration of model of a coriolis meter having aerated fluid flowing therethrough that accounts for compressibility inhomogeniety of the aerated fluid, in accordance with the present invention.

Models were presented for the effects of aeration on vibrating tube density meters in which the effects of compressibility and inhomogeniety were addressed independently. FIG. 16 shows a schematic of a lumped parameter model that incorporates the effects of compressibility and inhomogeniety using the mechanism-specific models developed above. The purpose of this model is to illustrate trends and parametric dependencies associated with aeration, it is not intended as a quantitative predictive tool.

The equations of motion of the above lumped parameter model, assuming solutions in the form of $e^{ST}$ where s is the complex frequency, can be expressed in non-dimensional form as:

$$\begin{bmatrix} A_{11} & A_{12} \\ A_{21} & A_{22} \end{bmatrix} \begin{Bmatrix} y_1 \\ x_1 \\ y_2 \\ x_2 \\ y_3 \\ x_3 \\ q_1 \\ z_1 \\ q_2 \\ z_2 \\ q_3 \\ z_3 \end{Bmatrix} = \{0\}$$

where:

$$A_{11} \equiv \begin{bmatrix} s + 2\zeta_f \alpha Q + 2\zeta_s & 1 + \alpha Q^2 + \Gamma & -2\zeta_f \alpha Q & -\alpha Q^2 & 0 & 0 \\ -1 & s & 0 & 0 & 0 & 0 \\ -\dfrac{2\zeta_f Q}{1-3\varphi} & -\dfrac{Q^2}{1-3\varphi} & s + \dfrac{2\zeta_f Q}{1-3\varphi} + \dfrac{2\zeta_g(2\varphi)}{1-3\varphi} + 2U_{ND} & \dfrac{Q^2}{1-3\varphi} & -\dfrac{2\zeta_s(2\varphi)}{1-3\varphi} & 0 \\ 0 & 0 & -1 & s & 0 & 0 \\ 0 & 0 & 0 & \dfrac{-2\zeta_g}{2\varphi} & s + \dfrac{2\zeta_g}{2\varphi} + 2U_{ND} & 0 \\ 0 & 0 & 0 & 0 & -1 & s \end{bmatrix}$$

$$A_{22} \equiv \begin{bmatrix} s + 2\zeta_f \alpha Q + 2\zeta_s & 1 + \alpha Q^2 + \Gamma & -2\zeta_f \alpha Q & -\alpha Q^2 & 0 & 0 \\ -1 & s & 0 & 0 & 0 & 0 \\ -\dfrac{2\zeta_f Q}{1-3\varphi} & -\dfrac{Q^2}{1-3\varphi} & s + \dfrac{2\zeta_f Q}{1-3\varphi} + \dfrac{2\zeta_g(2\varphi)}{1-3\varphi} - 2U_{ND} & \dfrac{Q^2}{1-3\varphi} & -\dfrac{2\zeta_s(2\varphi)}{1-3\varphi} & 0 \\ 0 & 0 & -1 & s & 0 & 0 \\ 0 & 0 & 0 & \dfrac{-2\zeta_g}{2\varphi} & s + \dfrac{2\zeta_g}{2\varphi} - 2U_{ND} & 0 \\ 0 & 0 & 0 & 0 & -1 & s \end{bmatrix}$$

-continued $$A_{12} = A_{21} \equiv \begin{bmatrix} 0 & -\Gamma & 0 & 0 & 0 & 0 \\ 0 & 0 & 0 & 0 & 0 & 0 \\ 0 & 0 & 0 & 0 & 0 & 0 \\ 0 & 0 & 0 & 0 & 0 & 0 \\ 0 & 0 & 0 & 0 & 0 & 0 \\ 0 & 0 & 0 & 0 & 0 & 0 \end{bmatrix}$$

The additional non-dimensional parameters that govern the dynamic response of the aeroelastic model compared to the quasi-steady model are defined in Table 4.

Solving the twelfth-order eigenvalue problem described above provides a means to assess the influence of the various parameters ability of the coriolis meter to measure the mass flow and density of a fluid under a variety of operating conditions.

Figure 17:
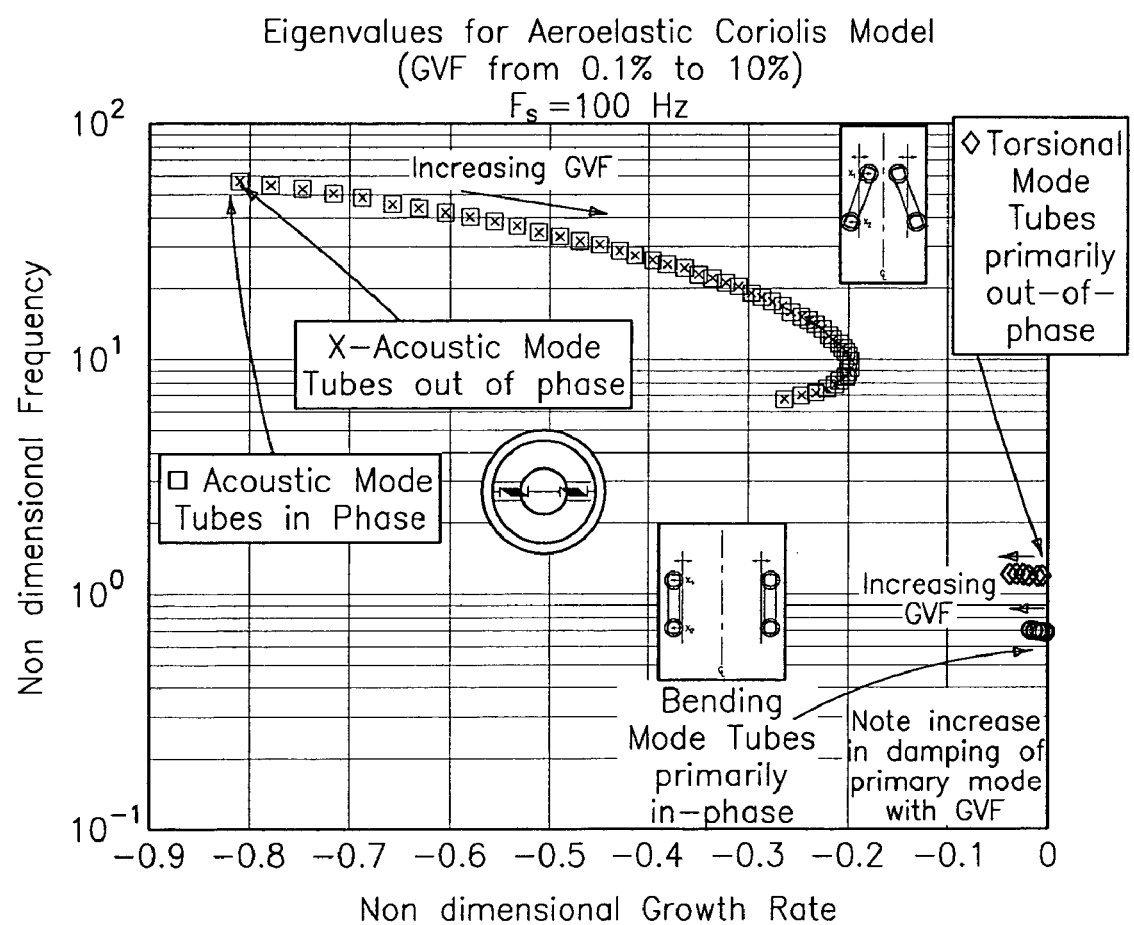
FIG. 17 is a plot of the eigenvalues for an aeroelastic coriolis model in accordance with the present invention.

The eigenvalues for the standard coriolis meter described in Tables 1-5 are shown in FIG. 17 as a function of gas volume fraction. Arrows indicate the movement of the eigenvalues as a function of gas volume fraction as the gas volume fraction is increased from 0.1% to 10%. The model shows four lightly damped modes, two corresponding to the modes present in the quasisteady model, and two primarily associated with the acoustic modes within the tubes. At low gas volume fraction (0.1% in this case), the oscillatory frequency of the acoustic modes is well above that of the structural modes, (~60 times the structural frequency in this case).

TABLE 5

Parameters Defining the Baseline Vibrating Tube Density Meter

| Parameter | Description | Value |
|---|---|---|
| $\zeta_{struct}$ | Critical Damping Ratio - structure | 0.01 |
| $\zeta_{fluid}$ | Critical Damping Ratio - fluid | 0.01 |
| $\zeta_{gas}$ | Critical Damping Ratio - gas | 1.0 |
| Q | Frequency Ratio | As determined by sound speed of air/water at STP and structural parameters |
| D | Tube diameter | 1.0 inches |

However, as the gas volume fraction is increased, the primarily acoustic modes move toward the primarily structural modes and compressibility of the fluid begins to influence the dynamics of the structural mode. Also, as the gas volume fraction increases, the natural frequency of the primarily bending mode is shown to increase as well, consistent with the quasi-steady effect of decreased mixture density.

The movement of the eigenvalues also indicates that the damping of the primary bending mode increases with gas volume fraction as well, consistent with commonly observed increase in drive gain required to maintain a constant amplitude oscillation in commercial coriolis meters subjected to entrained gases.

Figure 18:
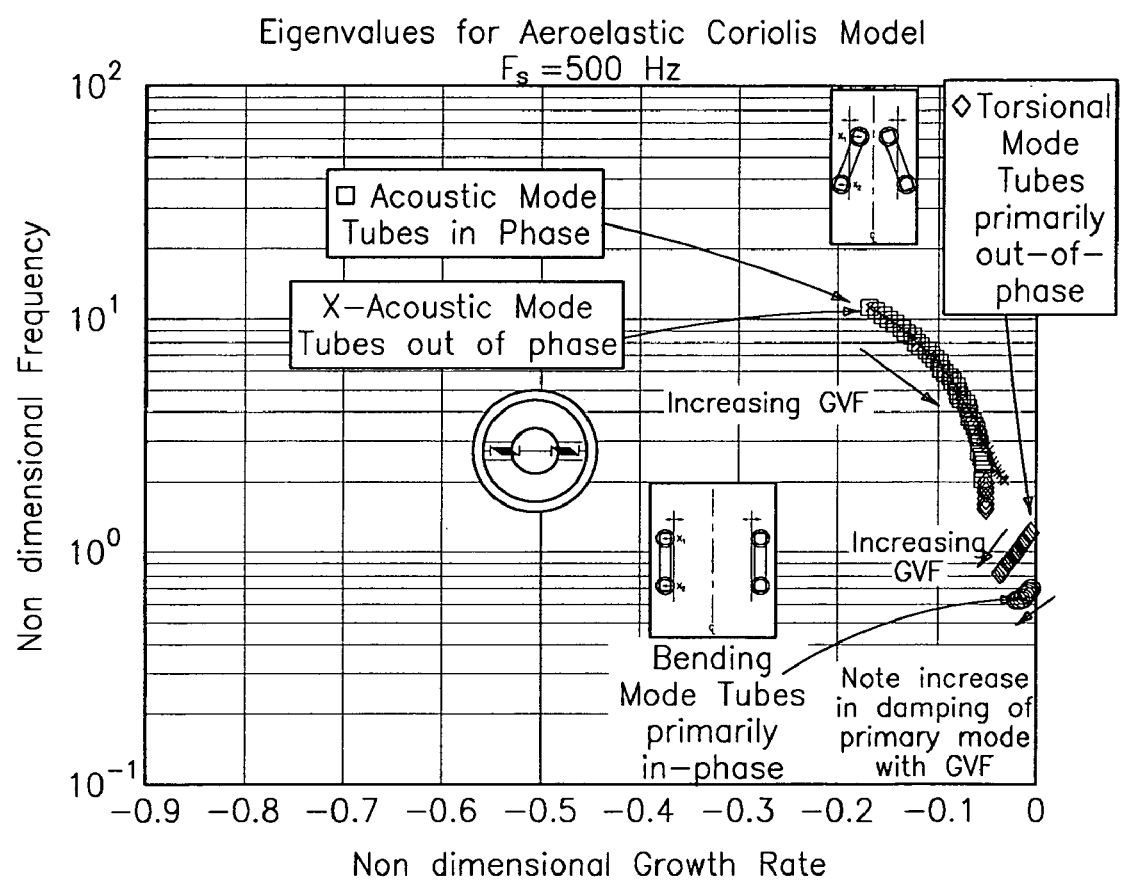
FIG. 18 is a plot of the eigenvalues for an aeroelastic coriolis model in accordance with the present invention.

FIG. 18 shows the eigenvalues for a Coriolis meter operating at significantly higher tube frequencies, all the other parameters are identical. As shown, the locations of the eigenvalues of the various modes are in much closer proximity, indicative of significantly higher level of aeroelastic interaction. Note that the higher structural frequency is reflected in the non-dimensional frequency of the "acoustic modes", approaching 10 in the limit of no gas and decreasing to approximately 1 at 10% GVF.

Figure 19:
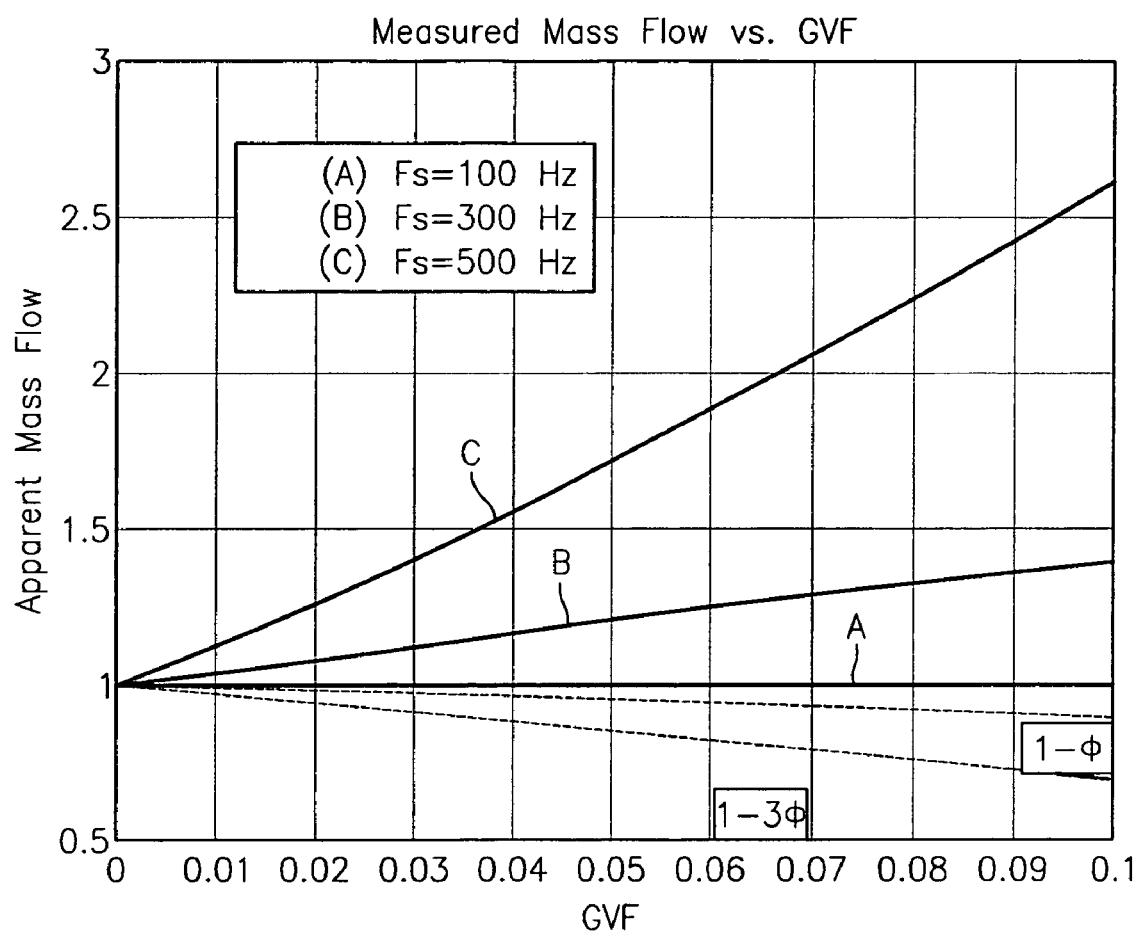
FIG. 19 is a plot of the measured mass flow rate as a function of the gas volume fraction in accordance with the present invention.

The lumped-parameter model can be used to estimate the errors that would result from using a quasi-steady calibration (i.e. non-aerated fluid) on a meter operating in aerated fluids. FIG. 19 shows the mass flow observed based on a quasi-steady interpretation of the phase shift in the primary bending mode as a function of gas volume fraction.

As shown, the model predicts that the coriolis meter operating with the lowest frequency tubes reports a mass flow measurement that is in good agreement with the actual mass flow over the range of gas volume fraction evaluated. However, for the higher frequency tubes, aeroelastic interactions associated with the increased compressibility and the inhomogeneity of the fluid result in significant errors between the actual and the interpreted mass flow rates. The "1-GVF" and "1-3GVF" lines are shown for reference purposes.

For the density measurement, the natural frequency of the primary tube bending mode predicted by the eigenvalue analysis is input into the frequency/density from the quasi-steady, homogeneous model to determine the apparent density of the fluid as follows.

$$\rho_{apparent} = \frac{\rho_{liq}}{a}\left(\frac{f_s^2}{f_{observed}^2} - 1\right)$$

Figure 20:
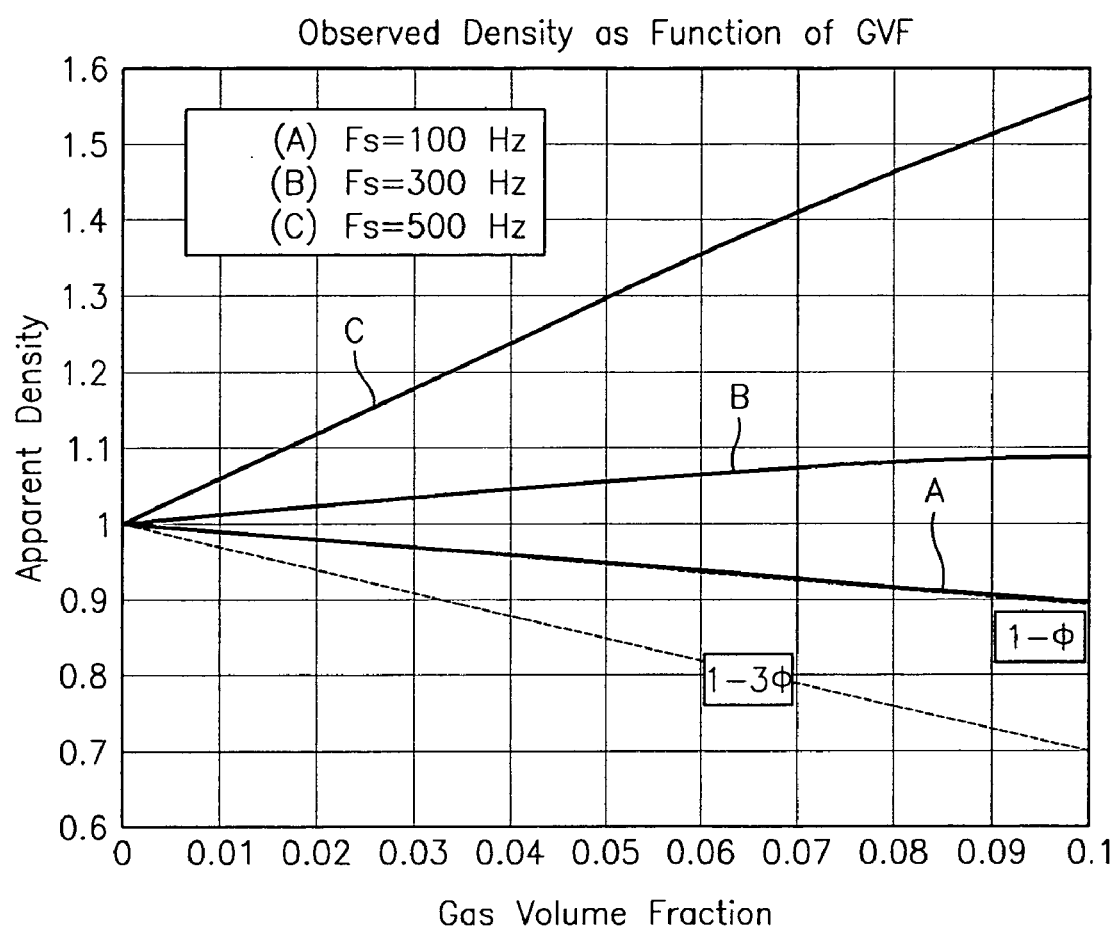
FIG. 20 is a plot of the observed density as a function of the gas volume fraction in accordance with the present invention.

FIG. 20 shows similar results for the density measurement. The coriolis meter with the lowest frequency tubes accurately reports the mixture density (1-GVF). The higher frequency tube designs are shown to report significant errors with increasing gas volume fraction.

As discussed hereinbefore, it is well known that entrained gases negatively impact the accuracy of coriolis meters. One aspect of the invention is described that uses two (or more) measurements of the speed of sound within vibrating tubes of a coriolis meter to improve the accuracy of the meter in the face of entrained gases.

For a given gas/liquid mixture flowing in a pipe, many factors can influence the in-situ gas volume fraction of the mixture, as discussed hereinbefore. Line pressure can have a large impact on the gas volume fraction at a given location in a pipe. Gas volume fraction changes with pressure because the gas is typically highly compressible and the liquid is not. For example, consider a well mixed mixture of 5% air in water at 30 psia. The gas volume fraction increases with decreasing pressure at a rate that is directly related to the line pressure. Assuming no gas comes out of solution, for simplicity, this mixture would have a gas volume fraction of approximately 10% if the pressure drops to 15 psia. This mechanism can result in significant changes in the gas volume fraction as a mixture flows through a coriolis meter, resulting in higher GVF levels in the downstream leg of the meter.

Slip velocity of bubbles can also result in variations in GVF in the legs of a Coriolis meter. Bubbles rise due to buoyancy. Therefore, the gas in a downward flowing leg with "hold-up" compared to that in an upward flowing leg, resulting in higher gas volume fractions in the downward flow leg than that in the upward.

The effect of this imbalance can seriously degrade the performance of a coriolis meter. In one aspect of the present invention the speed of sound is measured in each leg of a coriolis meter to aid in interpreting the traditional direct measurements, ie the phase lag in the tubes and the natural frequency of the tubes, in terms of mixture mass flow and density.

Figure 21:
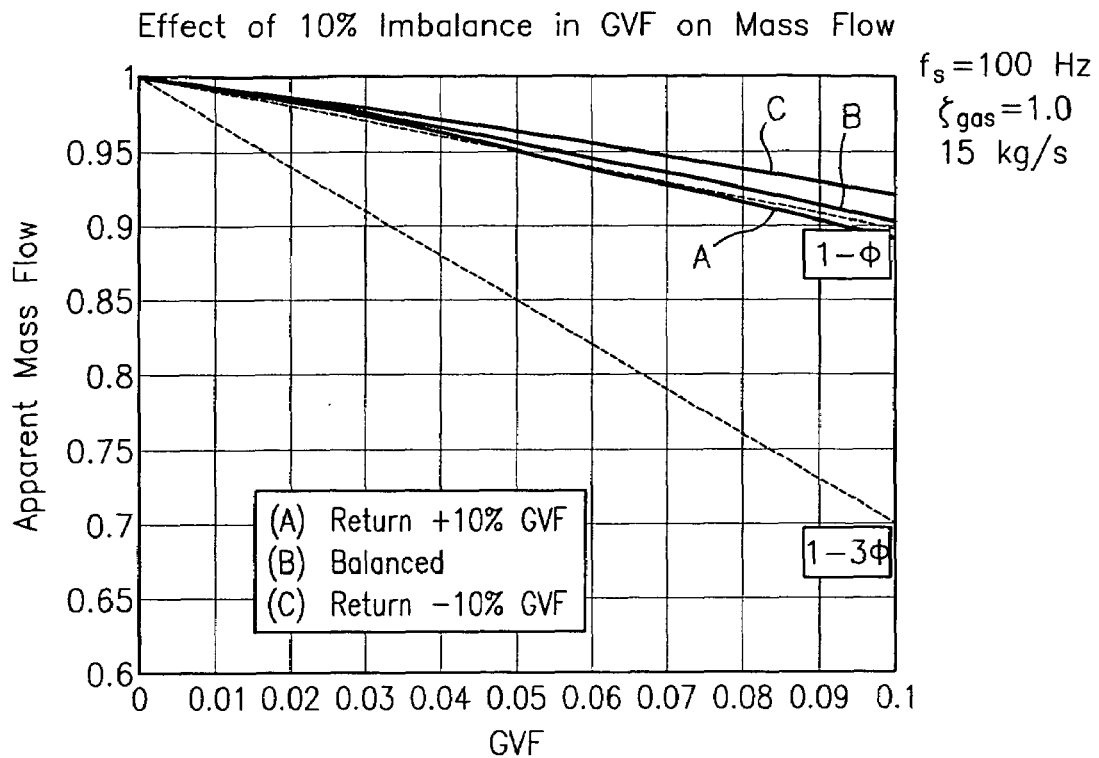
FIG. 21 is a plot of the apparent mass flow as a function of the gas volume fraction when a 10% imbalance in gas volume fraction between the tubes is present in accordance with the present invention.
Figure 22:
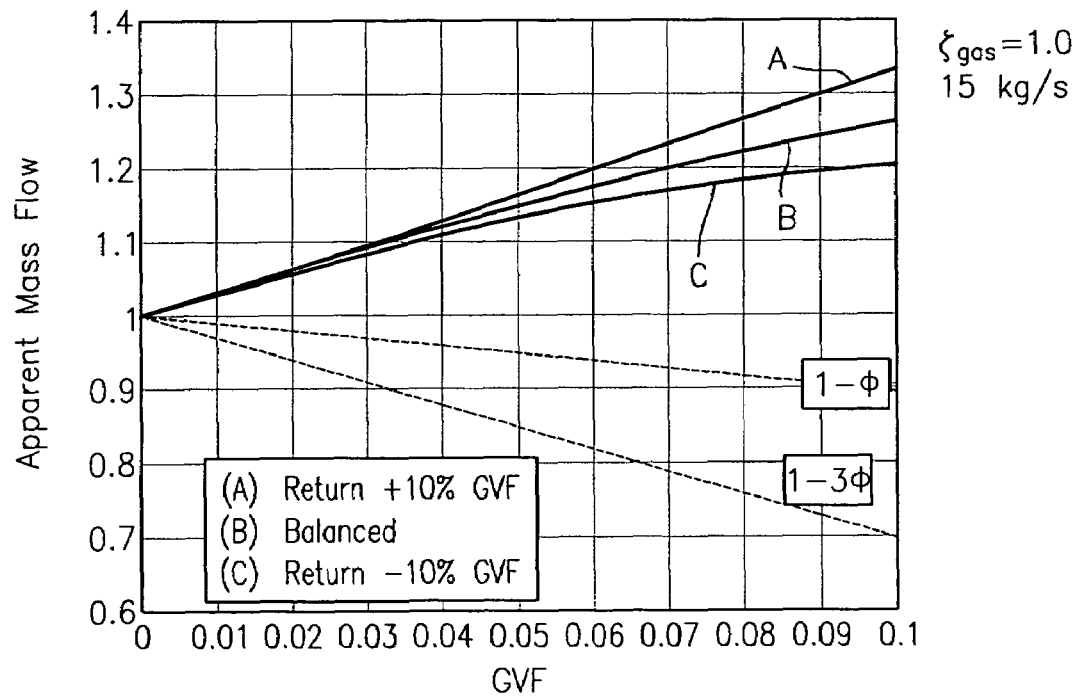
FIG. 22 is a plot of the apparent mass flow as a function of the gas volume fraction when a 10% imbalance in gas volume fraction between the tubes is present in accordance with the present invention.

FIGS. 21 and 22 shows the effect of gas volume fraction on the mass flow measurement of representative coriolis meters. The charts shows that imbalance of 10% of the GVF in the vibrating tubes has a significant impact. For this example, knowledge of the imbalance and knowledge of the average GVF in terms of measurement accuracy may be used to augment the coriolis meter.

Figure 27:
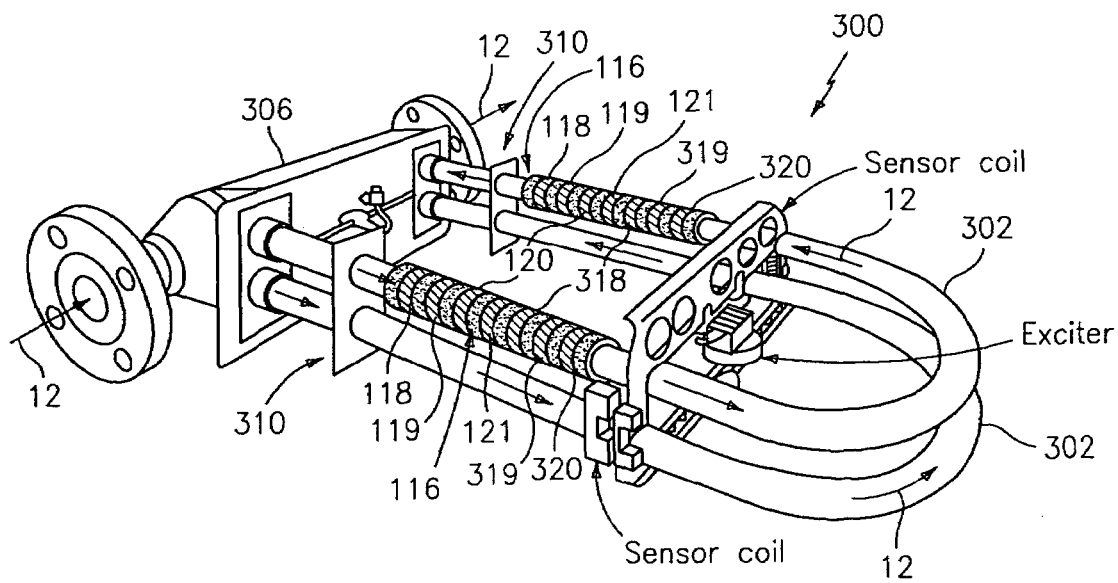
FIG. 27 is a perspective view of a coriolis meter having a pair of sensor arrays disposed on the outward flow portion of a tube and the inward flow portion of the tube, respectively, in accordance with the present invention.

In this embodiment of the present invention as shown in FIGS. 4 and 27, strain based sensors are disposed on each tube similar to that described hereinafter, that use sonar-based methods to measure the speed of sound in each tube, infer a GVF in each tube, and use this knowledge in conjunction with empirical or analytical models, as described hereinbefore, to improve both the mass flow and density measurement of coriolis based flow meters.

FIG. 23 illustrates a gas volume fraction meter 100 of FIG. 2, as described herein before. The GVF meter 100 includes a sensing device 116 disposed on the pipe 14 and a processing unit 124. The sensing device 116 comprises an array of strain-based sensors or pressure sensors 118-121 for measuring the unsteady pressures produced by acoustic waves propagating through the flow 12 to determine the speed of sound (SOS). The pressure signals $P_1(t)$-$P_N(t)$ are provided to the processing unit 124, which digitizes the pressure signals and computes the SOS and GVF parameters. A cable 113 electronically connects the sensing device 116 to the processing unit 124. The analog pressure sensor signals $P_1(t)$-$P_N(t)$ are typically 4-20 mA current loop signals.

The array of pressure sensors 118-121 comprises an array of at least two pressure sensors 118,119 spaced axially along the outer surface 122 of the pipe 14, having a process flow 112 propagating therein. The pressure sensors 118-121 may be clamped onto or generally removably mounted to the pipe by any releasable fastener, such as bolts, screws and clamps. Alternatively, the sensors may be permanently attached to, ported in or integral (e.g., embedded) with the pipe 14. The array of sensors of the sensing device 116 may include any number of pressure sensors 118-121 greater than two sensors, such as three, four, eight, sixteen or N number of sensors between two and twenty-four sensors. Generally, the accuracy of the measurement improves as the number of sensors in the array increases. The degree of accuracy provided by the greater number of sensors is offset by the increase in complexity and time for computing the desired output parameter of the flow. Therefore, the number of sensors used is dependent at least on the degree of accuracy desired and the desire update rate of the output parameter provided by the apparatus 100. The pressure sensors 118-119 measure the unsteady pressures produced by acoustic waves propagating through the flow, which are indicative of the SOS propagating through the fluid flow 12 in the pipe. The output signals ($P_1(t)$-$P_N(t)$) of the pressure sensors 118-121 are provided to a pre-amplifier unit 139 that amplifies the signals generated by the pressure sensors 118-121. The processing unit 124 processes the pressure measurement data $P_1(t)$-$P_{N,N}(t)$ and determines the desired parameters and characteristics of the flow 12, as described hereinbefore.

The apparatus 100 also contemplates providing one or more acoustic sources 127 to enable the measurement of the speed of sound propagating through the flow for instances of acoustically quiet flow. The acoustic source may be a device the taps or vibrates on the wall of the pipe, for example. The acoustic sources may be disposed at the input end of output end of the array of sensors 118-121, or at both ends as shown. One should appreciate that in most instances the acoustics sources are not necessary and the apparatus passively detects the acoustic ridge provided in the flow 12, as will be described in greater detail hereinafter. The passive noise includes noise generated by pumps, valves, motors, and the turbulent mixture itself.

As suggested and further described in greater detail hereinafter, the apparatus 10 has the ability to measure the speed of sound (SOS) by measuring unsteady pressures created by acoustical disturbances propagating through the flow 12. Knowing or estimating the pressure and/or temperature of the flow and the speed of sound of the acoustic disturbances or waves, the processing unit 124 can determine gas volume fraction, such as that described in U.S. patent application Ser. No. 10/349,716 (CiDRA Docket No. CC-0579), filed Jan. 23, 2003, U.S. patent application Ser. No. 10/376,427 (CiDRA Docket No. CC-0596), filed Feb. 26, 2003, U.S. patent application Ser. No. 10/762,410 (CiDRA Docket No. CC-0703), filed Jan. 21, 2004, which are all incorporated by reference.

Similar to the apparatus 100 of FIG. 23, an apparatus 200 of FIG. 24 embodying the present invention has an array of at least two pressure sensors 118,119, located at two locations $x_1,x_2$ axially along the pipe 14 for sensing respective stochastic signals propagating between the sensors 118,119 within the pipe at their respective locations. Each sensor 118,119 provides a signal indicating an unsteady pressure at the location of each sensor, at each instant in a series of sampling instants. One will appreciate that the sensor array may include more than two pressure sensors as depicted by pressure sensor 120,121 at location $x_3,x_N$. The pressure generated by the acoustic pressure disturbances may be measured through strained-based sensors and/or pressure sensors 118-121. The pressure sensors 118-121 provide analog pressure time-varying signals $P_1(t),P_2(t),P_3(t),P_N(t)$ to the signal processing unit 124. The processing unit 124 processes the pressure signals to first provide output signals 151,155 indicative of the speed of sound propagating through the flow 12, and subsequently, provide a GVF measurement in response to pressure disturbances generated by acoustic waves propagating through the flow 12.

The processing unit 124 receives the pressure signals from the array of sensors 118-121. A data acquisition unit 154 digitizes pressure signals $P_1(t)$-$P_N(t)$ associated with the acoustic waves 14 propagating through the pipe 114. An FFT logic 156 calculates the Fourier transform of the digitized time-based input signals $P_1(t)$-$P_N(t)$ and provide complex frequency domain (or frequency based) signals $P_1(\omega),P_2(\omega),P_3(\omega),P_N(\omega)$ indicative of the frequency content of the input signals.

A data accumulator 158 accumulates the additional signals $P_1(t)$-$P_N(t)$ from the sensors, and provides the data accumulated over a sampling interval to an array processor 160, which performs a spatial-temporal (two-dimensional) transform of the sensor data, from the xt domain to the k-ω domain, and then calculates the power in the k-ω plane, as represented by a k-ω plot, similar to that provided by the convective array processor 146.

To calculate the power in the k-ω plane, as represented by a k-ω plot (see FIG. 25) of either the signals or the differenced signals, the array processor 160 determines the wavelength and so the (spatial) wavenumber k, and also the (temporal) frequency and so the angular frequency ω, of various of the spectral components of the stochastic parameter. There are numerous algorithms available in the public domain to perform the spatial/temporal decomposition of arrays of sensor units 118-121.

Figure 25:
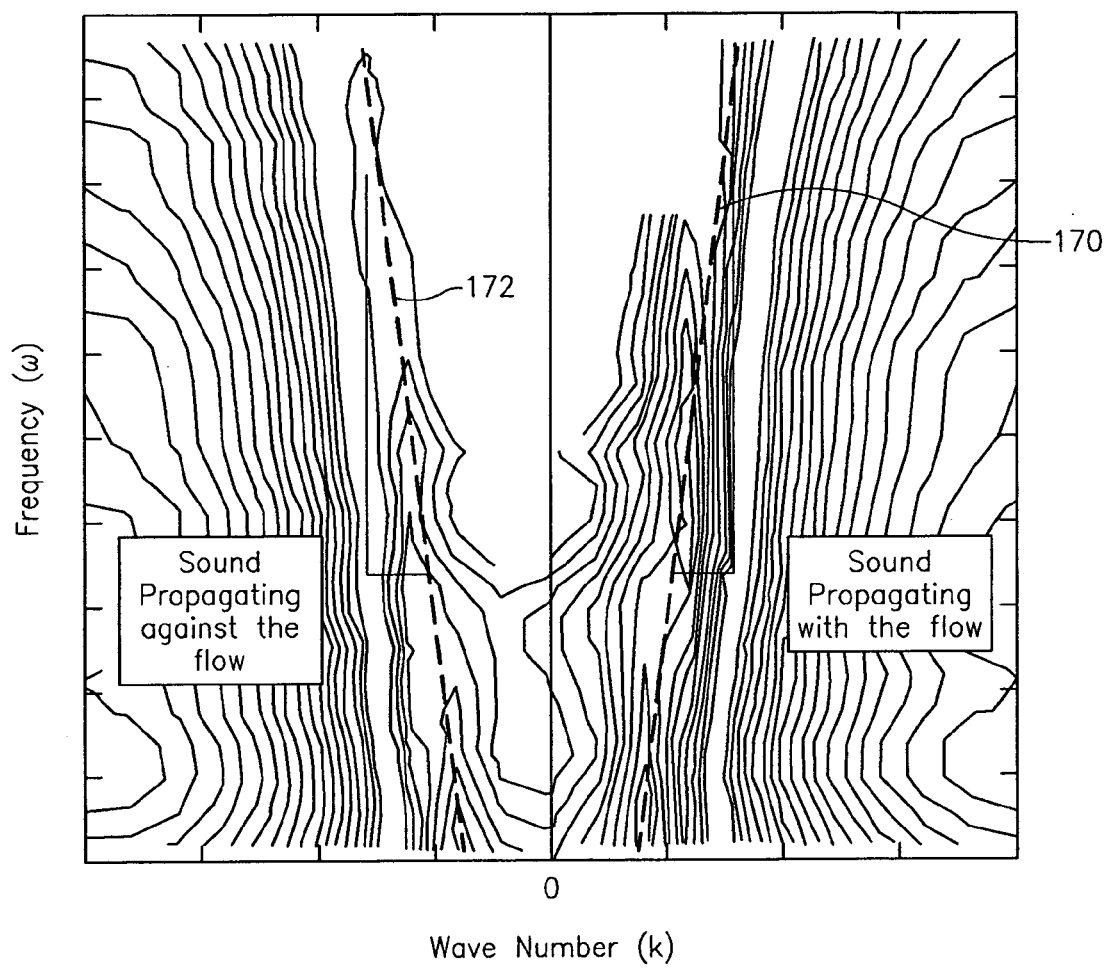
FIG. 25 is a kω plot of data processed from an array of pressure sensors use to measure the speed of sound of a fluid flow passing in a pipe, in accordance with the present invention.

In the case of suitable acoustic waves being present in both axial directions, the power in the k-ω plane shown in a k-ω plot of FIG. 25 so determined will exhibit a structure that is called an acoustic ridge 170,172 in both the left and right planes of the plot, wherein one of the acoustic ridges 170 is indicative of the speed of sound traveling in one axial direction and the other acoustic ridge 172 being indicative of the speed of sound traveling in the other axial direction. The acoustic ridges represent the concentration of a stochastic parameter that propagates through the flow and is a mathematical manifestation of the relationship between the spatial variations and temporal variations described above. Such a plot will indicate a tendency for k-ω pairs to appear more or less along a line 170,172 with some slope, the slope indicating the speed of sound.

The power in the k-ω plane so determined is then provided to an acoustic ridge identifier 162, which uses one or another feature extraction method to determine the location and orientation (slope) of any acoustic ridge present in the left and right k-ω plane. The velocity may be determined by using the slope of one of the two acoustic ridges 170,172 or averaging the slopes of the acoustic ridges 170,172.

Finally, information including the acoustic ridge orientation (slope) is used by an analyzer 164 to determine the flow parameters relating to measured speed of sound, such as the consistency or composition of the flow, the density of the flow, the average size of particles in the flow, the air/mass ratio of the flow, gas volume fraction of the flow, the speed of sound propagating through the flow, and/or the percentage of entrained air within the flow.

An array processor 160 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by $k=2\pi/\lambda$ where $\lambda$ is the wavelength of a spectral component, and corresponding angular frequencies given by $\omega=2\pi\upsilon$.

One such technique of determining the speed of sound propagating through the flow 12 is using array processing techniques to define an acoustic ridge in the k-ω plane as shown in FIG. 25. The slope of the acoustic ridge is indicative of the speed of sound propagating through the flow 12. The speed of sound (SOS) is determined by applying sonar arraying processing techniques to determine the speed at which the one dimensional acoustic waves propagate past the axial array of unsteady pressure measurements distributed along the pipe 14.

The apparatus 200 of the present invention measures the speed of sound (SOS) of one-dimensional sound waves propagating through the mixture to determine the gas volume fraction of the mixture. It is known that sound propagates through various mediums at various speeds in such fields as SONAR and RADAR fields. The speed of sound propagating through the pipe and flow 12 may be determined using a number of known techniques, such as those set forth in U.S. patent application Ser. No. 09/344,094, filed Jun. 25, 1999, now U.S. Pat. No. 6,354,147; U.S. patent application Ser. No. 10/795,111, filed Mar. 4, 2004; U.S. patent application Ser. No. 09/997,221, filed Nov. 28, 2001, now U.S. Pat. No. 6,587,798; U.S. patent application Ser. No. 10/007,749, filed Nov. 7, 2001, and U.S. patent application Ser. No. 10/762,410, filed Jan. 21, 2004, each of which are incorporated herein by reference.

While the sonar-based flow meter using an array of sensors 118-121 to measure the speed of sound of an acoustic wave propagating through the mixture is shown and described, one will appreciate that any means for measuring the speed of sound of the acoustic wave may used to determine the entrained gas volume fraction of the mixture/fluid or other characteristics of the flow described hereinbefore.

The analyzer 164 of the processing unit 124 provides output signals indicative of characteristics of the process flow 12 that are related to the measured speed of sound (SOS) propagating through the flow 12. For example, to determine the gas volume fraction (or phase fraction), the analyzer 164 assumes a nearly isothermal condition for the flow 12. As such the gas volume fraction or the void fraction is related to the speed of sound by the following quadratic equation:

$$Ax^2+Bx+C=0$$

wherein x is the speed of sound, $A=1+rg/rl*(K_{eff}/P-1)-K_{eff}/P$, $B=K_{eff}/P-2+rg/rl$; $C=1-K_{eff}/rl*a_{meas}^2$); Rg=gas density, rl=liquid density, $K_{eff}$=effective K (modulus of the liquid and pipewall), P=pressure, and $a_{meas}$=measured speed of sound.

Effectively, $$\text{Gas Voulume Fraction } (GVF)=(-B+sqrt(B^2-4*A*C))/(2*A)$$

Alternatively, the sound speed of a mixture can be related to volumetric phase fraction ($\phi_i$) of the components and the sound speed (a) and densities (ρ) of the component through the Wood equation.

$$\frac{1}{\rho_{mix} a_{mix\infty}^2} = \sum_{i=1}^{N} \frac{\phi_i}{\rho_i a_i^2} \text{ where } \rho_{mix} = \sum_{i=1}^{N} \rho_i \phi_i$$

One dimensional compression waves propagating within a flow 12 contained within a pipe 14 exert an unsteady internal pressure loading on the pipe. The degree to which the pipe displaces as a result of the unsteady pressure loading influences the speed of propagation of the compression wave. The relationship among the infinite domain speed of sound and density of a mixture; the elastic modulus (E), thickness (t), and radius (R) of a vacuum-backed cylindrical conduit; and the effective propagation velocity ($a_{eff}$) for one dimensional compression is given by the following expression:

$$a_{eff} = \frac{1}{\sqrt{\frac{1}{a_{mix\infty}^2} + \rho_{mix}\frac{2R}{Et}}} \quad (eq\ 1)$$

Figure 26:
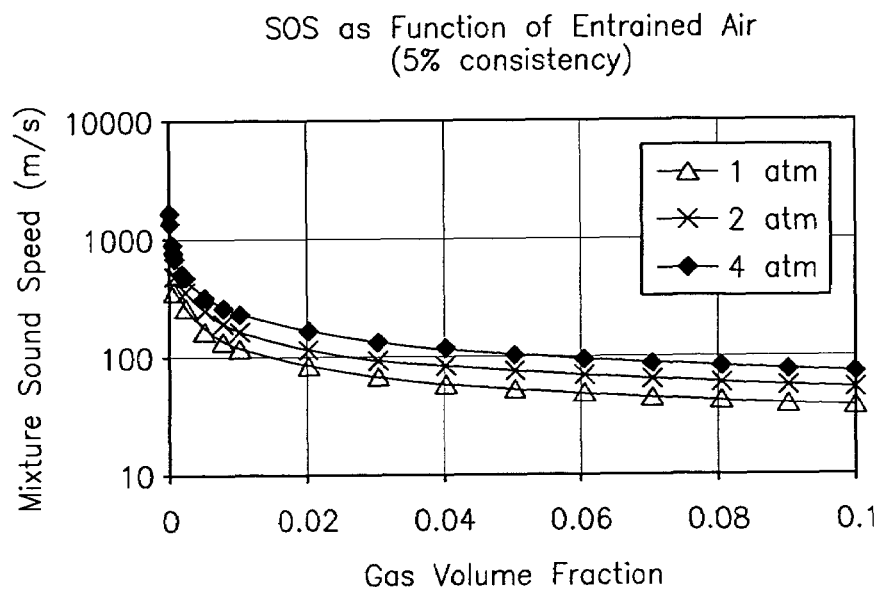
FIG. 26 is a plot of the speed of sound of the fluid flow as a function of the gas volume fraction over a range of different pressures, in accordance with the present invention.

The mixing rule essentially states that the compressibility of a mixture $(1/(\rho a^2))$ is the volumetrically-weighted average of the compressibilities of the components. For gas/liquid mixtures 12 at pressure and temperatures typical of paper and pulp industry, the compressibility of gas phase is orders of magnitudes greater than that of the liquid. Thus, the compressibility of the gas phase and the density of the liquid phase primarily determine mixture sound speed, and as such, it is necessary to have a good estimate of process pressure to interpret mixture sound speed in terms of volumetric fraction of entrained gas. The effect of process pressure on the relationship between sound speed and entrained air volume fraction is shown in FIG. 26.

Some or all of the functions within the processing unit 24 may be implemented in software (using a microprocessor or computer) and/or firmware, or may be implemented using analog and/or digital hardware, having sufficient memory, interfaces, and capacity to perform the functions described herein.

While the embodiments of the present invention shown in FIGS. 2, 23 and 24 shown the pressure sensors 118-121 disposed on the pipe 14, separate from the coriolis meter, the present invention contemplates that the GVF meter 100 may be integrated with the coriolis meter to thereby provide a single apparatus as shown in FIGS. 27 and 29. As shown in these Figures, the pressure sensors 118-121 may be disposed on one or both of the tubes 302 of the coriolis meters 300, 310.

Referring to FIG. 27, a dual tube 302 coriolis meter 300 is provided having an array of pressure sensors 118-121, 318-320 disposed on a tube 302 of the coriolis meter. In this embodiment, an array of piezoelectric material strip or sensors 118-121,318-320 are disposed on a web and clamped onto the tube 302 as a unitary wrap. This configuration is similar to that described in U.S. patent application Ser. No. 10/795,111, filed on Mar. 4, 2004, which is incorporated herein by reference. Similar to that described herein before as shown in FIGS. 23 and 24, the pressure signals are provided to a processing unit to calculate at least one of the SOS, GVF and reduced frequency. As shown, the coriolis meter 300 includes an array of sensor disposed on the outward flow portion and inward flow portion of one of the tubes 302 of the meter 300. Each array providing signals that are processed in accordance with the invention as described hereinbefore to provide at least one of the SOS, GVF and reduced frequency. Knowing these parameters at the outward and inward portions of a tube 302, the mass flow and/or density measurement of the coriolis meter may be augmented to compensated for entrained gas in the fluid flow 12.

The flow tubes 302 employed in Coriolis meter are many and varied. Typically the flow is diverted from the center line of the pipe to which the coriolis meter is attached, however, Coriolis meters employing straight tubes, in line with the process pipe, have also been introduced. Despite the varied shapes, coriolis flow tubes are typical long and relatively slender, bent or straight. For bent tube coriolis meters, the flow tubes are typically of constant and reduced, cross-sectional than the pipe 14 to which the meter is attached, resulting in increased fluid velocity through the flow tubes. These two characteristics make the flow tubes well suited as an acoustic waveguide for low frequency acoustic waves.

Low frequency acoustic waves refer to waves for which the wavelength is significantly larger than the diameter of the flow tube 302. As we will see, for coriolis flow tubes, typically on the order of 1 inch in diameter, this definition of low frequency is not very restrictive. Thus, for a 1 inch diameter flow tube conveying water, the acoustic waves with frequencies significantly below 60,000 hz are considered low frequency (1 inch*(1 ft/12 inches)*5000 ft/sec)

For these low frequency waves, the bends in the coriolis flow tubes 302 do not have any significant effect on the propagation velocity of the acoustics. Thus, the coriolis flow tubes 302 are well suited to serve as the waveguide on which to deploy and array of sensors with which to determine the speed of sound of the mixture.

Most coriolis meters have highly tuned, well balanced sets of flow tubes. It is important to minimize any impact of the sensor on the dynamics of the flow tubes. For the U-tube shown in FIG. 27, the array of sensors may be deployed near the body 306 of the meter where the tubes 302 are essentially cantilevered at 310. By attaching lightweight, strain based sensors 118-121 at this position, the dynamics of the flow tube should be essentially unaffected by the sensor array. Further, placing the two groups of sensors 118,119 and 120,121 at the ends allows the sensor array aperture to span the entire flow tube. Instrumenting the flow tubes as described herein maximize the aperture of the sensor array contained within a coriolis meter.

While integrated coriolis meters 300 of FIG. 27 are U-shaped, the present invention contemplates that the sensor array may similarly disposed on a tube of a straight tube coriolis meter.

While the array of sensors is provided on the outward and inward flow portions of one of the tubes to compensate for aerated fluid flow, it is contemplate that the sensor arrays may be disposed on pipe 14 at the input and output ends, respectively, of the coriolis meter to provide representative SOS, GVF and reduced frequency at the outward and inward flow portions of a tube 302.

For any embodiments described herein, the pressure sensors, including electrical strain gages, optical fibers and/or gratings among others as described herein, may be attached to the pipe by adhesive, glue, epoxy, tape or other suitable attachment means to ensure suitable contact between the sensor and the pipe. The sensors may alternatively be removable or permanently attached via known mechanical techniques such as mechanical fastener, spring loaded, clamped, clam shell arrangement, strapping or other equivalents. Alternatively, the strain gages, including optical fibers and/or gratings, may be embedded in a composite pipe. If desired, for certain applications, the gratings may be detached from (or strain or acoustically isolated from) the pipe if desired.

It is also within the scope of the present invention that any other strain sensing technique may be used to measure the variations in strain in the pipe, such as highly sensitive piezoelectric, electronic or electric, strain gages attached to or embedded in the pipe. Accelerometers may be also used to measure the unsteady pressures. Also, other pressure sensors may be used, as described in a number of the aforementioned patents, which are incorporated herein by reference.

In another embodiment, the sensor may comprise of piezofilm or strips (e.g. PVDF) as described in at least one of the aforementioned patent applications.

While the illustrations show four sensors mounted or integrated in a tube of the coriolis meter, the invention contemplates any number of sensors in the array as taught in at least one of the aforementioned patent applications. Also the invention contemplates that the array of sensors may be mounted or integrated with a tube of a coriolis meter having shape, such as pretzel shape, U-shaped (as shown), straight tube and any curved shape.

The invention further contemplated providing an elongated, non-vibrating (or oscillating) portion that permits a greater number of sensors to be used in the array.

While the present invention describes an array of sensors for measuring the speed of sound propagating through the flow for use in interpreting the relationship between coriolis forces and the mass flow through a coriolis meter. Several other methods exists.

For example, for a limited range of fluids, an ultrasonic device could be used to determine speed of sound of the fluid entering. It should be noted that the theory indicates that the interpretation of coriolis meters will be improved for all fluids if the sound speed of the process fluid is measured and used in the interpretation. Thus, knowing that the sound speed of the fluid is 5000 ft/sec as it would be for a water like substance, compared to 1500 ft/sec as it would be for say supercritical ethylene, would improve the performance of a coriolis based flow and density measurement. These measurements could be performed practically using existing ultrasonic meters.

Another approach to determine speed of sound of the fluids is to measure the resonant frequency of the acoustic modes of the flow tubes. When installed in a flow line, the cross sectional area changes associated with the transition from the pipe into the typically much smaller flow tubes creates a significant change in acoustic impedance. As a result of this change in impedance, the flow tube act as somewhat of a resonant cavity. By tracking the resonant frequency of this cavity, one could determine the speed of sound of the fluid occupying the cavity. This could be performed with a single pressure sensitive device, mounted either on the coriolis meter, of on the piping network attached to the coriolis meter.

In a more general aspect, the present invention contemplates the ability to augmenting the performance of a coriolis meter using any method or means for measuring the gas volume fraction of the fluid flow.

In one embodiment of the present invention as shown in FIG. 23, each of the pressure sensors 118-121 may include a piezoelectric film sensor to measure the unsteady pressures of the fluid flow 12 using either technique described hereinbefore.

The piezoelectric film sensors include a piezoelectric material or film to generate an electrical signal proportional to the degree that the material is mechanically deformed or stressed. The piezoelectric sensing element is typically conformed to allow complete or nearly complete circumferential measurement of induced strain to provide a circumferential-averaged pressure signal. The sensors can be formed from PVDF films, co-polymer films, or flexible PZT sensors, similar to that described in "Piezo Film Sensors Technical Manual" provided by Measurement Specialties, Inc., which is incorporated herein by reference. A piezoelectric film sensor that may be used for the present invention is part number 1-1002405-0, LDT4-028K, manufactured by Measurement Specialties, Inc.

Piezoelectric film ("piezofilm"), like piezoelectric material, is a dynamic material that develops an electrical charge proportional to a change in mechanical stress. Consequently, the piezoelectric material measures the strain induced within the pipe 14 due to unsteady pressure variations (e.g., acoustic waves) within the process mixture 12. Strain within the pipe is transduced to an output voltage or current by the attached piezoelectric sensor. The piezoelectrical material or film may be formed of a polymer, such as polarized fluoropolymer, polyvinylidene fluoride (PVDF). The piezoelectric film sensors are similar to that described in U.S. patent application Ser. No. 10/712,818 (CiDRA Docket No. CC-0675), U.S. patent application Ser. No. 10/712,833 (CiDRA Docket No. CC-0676), and U.S. patent application Ser. No. 10/795,111 (CiDRA Docket No. CC-0732), which are incorporated herein by reference.

Another embodiment of the present invention include a pressure sensor such as pipe strain sensors, accelerometers, velocity sensors or displacement sensors, discussed hereinafter, that are mounted onto a strap to enable the pressure sensor to be clamped onto the pipe. The sensors may be removable or permanently attached via known mechanical techniques such as mechanical fastener, spring loaded, clamped, clam shell arrangement, strapping or other equivalents. These certain types of pressure sensors, it may be desirable for the pipe 12 to exhibit a certain amount of pipe compliance.

Instead of single point pressure sensors 118-121, at the axial locations along the pipe 12, two or more pressure sensors may be used around the circumference of the pipe 12 at each of the axial locations. The signals from the pressure sensors around the circumference at a given axial location may be averaged to provide a cross-sectional (or circumference) averaged unsteady acoustic pressure measurement. Other numbers of acoustic pressure sensors and annular spacing may be used. Averaging multiple annular pressure sensors reduces noises from disturbances and pipe vibrations and other sources of noise not related to the one-dimensional acoustic pressure waves in the pipe 12, thereby creating a spatial array of pressure sensors to help characterize the one-dimensional sound field within the pipe 12.

The pressure sensors 118-121 of FIG. 23 described herein may be any type of pressure sensor, capable of measuring the unsteady (or ac or dynamic) pressures within a pipe 14, such as piezoelectric, optical, capacitive, resistive (e.g., Wheatstone bridge), accelerometers (or geophones), velocity measuring devices, displacement measuring devices, etc. If optical pressure sensors are used, the sensors 118-121 may be Bragg grating based pressure sensors, such as that described in U.S. patent application Ser. No. 08/925,598, entitled "High Sensitivity Fiber Optic Pressure Sensor For Use In Harsh Environments", filed Sep. 8, 1997, now U.S. Pat. No. 6,016,702, and in U.S. patent application Ser. No. 10/224,821, entitled "Non-Intrusive Fiber Optic Pressure Sensor for Measuring Unsteady Pressures within a Pipe", which are incorporated herein by reference. In an embodiment of the present invention that utilizes fiber optics as the pressure sensors 14 they may be connected individually or may be multiplexed along one or more optical fibers using wavelength division multiplexing (WDM), time division multiplexing (TDM), or any other optical multiplexing techniques.

In certain embodiments of the present invention, a piezoelectronic pressure transducer may be used as one or more of the pressure sensors 115-118 and it may measure the unsteady (or dynamic or ac) pressure variations inside the pipe or tube 14 by measuring the pressure levels inside of the tube. These sensors may be ported within the pipe to make direct contact with the mixture 12. In an embodiment of the present invention, the sensors 14 comprise pressure sensors manufactured by PCB Piezotronics. In one pressure sensor there are integrated circuit piezoelectric voltage mode-type sensors that feature built-in microelectronic amplifiers, and convert the high-impedance charge into a low-impedance voltage output. Specifically, a Model 106B manufactured by PCB Piezotronics is used which is a high sensitivity, acceleration compensated integrated circuit piezoelectric quartz pressure sensor suitable for measuring low pressure acoustic phenomena in hydraulic and pneumatic systems. It has the unique capability to measure small pressure changes of less than 0.001 psi under high static conditions. The 106B has a 300 mV/psi sensitivity and a resolution of 91 dB (0.0001 psi).

The pressure sensors incorporate a built-in MOSFET microelectronic amplifier to convert the high-impedance charge output into a low-impedance voltage signal. The sensor is powered from a constant-current source and can operate over long coaxial or ribbon cable without signal degradation. The low-impedance voltage signal is not affected by triboelectric cable noise or insulation resistance-degrading contaminants. Power to operate integrated circuit piezoelectric sensors generally takes the form of a low-cost, 24 to 27 VDC, 2 to 20 mA constant-current supply. A data acquisition system of the present invention may incorporate constant-current power for directly powering integrated circuit piezoelectric sensors.

Most piezoelectric pressure sensors are constructed with either compression mode quartz crystals preloaded in a rigid housing, or unconstrained tourmaline crystals. These designs give the sensors microsecond response times and resonant frequencies in the hundreds of kHz, with minimal overshoot or ringing. Small diaphragm diameters ensure spatial resolution of narrow shock waves.

The output characteristic of piezoelectric pressure sensor systems is that of an AC-coupled system, where repetitive signals decay until there is an equal area above and below the original base line. As magnitude levels of the monitored event fluctuate, the output remains stabilized around the base line with the positive and negative areas of the curve remaining equal.

It is also within the scope of the present invention that any strain sensing technique may be used to measure the variations in strain in the pipe, such as highly sensitive piezoelectric, electronic or electric, strain gages and piezo-resistive strain gages attached to the pipe 12. Other strain gages include resistive foil type gages having a race track configuration similar to that disclosed U.S. patent application Ser. No. 09/344,094, filed Jun. 25, 1999, now U.S. Pat. No. 6,354,147, which is incorporated herein by reference. The invention also contemplates strain gages being disposed about a predetermined portion of the circumference of pipe 12. The axial placement of and separation distance $\Delta X_1$, $\Delta X_2$ between the strain sensors are determined as described herein above.

It is also within the scope of the present invention that any other strain sensing technique may be used to measure the variations in strain in the tube, such as highly sensitive piezoelectric, electronic or electric, strain gages attached to or embedded in the tube 14.

While a number of sensor have been described, one will appreciate that any sensor the measures the speed of sound propagating through the fluid may be used with the present invention, including ultrasonic sensors.

The dimensions and/or geometries for any of the embodiments described herein are merely for illustrative purposes and, as such, any other dimensions and/or geometries may be used if desired, depending on the application, size, performance, manufacturing requirements, or other factors, in view of the teachings herein.

It should be understood that, unless stated otherwise herein, any of the features, characteristics, alternatives or modifications described regarding a particular embodiment herein may also be applied, used, or incorporated with any other embodiment described herein. Also, the drawings herein are not drawn to scale.

Although the invention has been described and illustrated with respect to exemplary embodiments thereof, the foregoing and various other additions and omissions may be made therein and thereto without departing from the spirit and scope of the present invention.

What is claimed is:

1. A flow measuring system for measuring the mass flow rate of an aerated fluid flowing in a pipe, the flow measuring system comprising:

a meter having a pair of vibrating tubes wherein fluid flows therethrough, the meter providing a phase signal indicative of a phase difference between the pair of tubes, said tubes having an inward flow portion and an outward flow portion;

a flow measuring device measuring the speed of sound propagating through the fluid at the inward flow portion and outward flow portion of a tube, the measuring device providing at least one of an SOS signal indicative of the speed of sound propagating through the fluid, a GVF signal indicative of the gas volume fraction of the fluid and a reduced frequency indicative of the reduced frequency of the fluid; and a processing unit determining a compensated mass flow rate measurement in response to at least one of the SOS signal, the GVF signal and the reduced frequency signal and the phase signal.

2. The measuring system of claim 1, wherein the speed of sound measurement is used to determine a gas volumetric fraction (GVF) in the flow of the fluid.

3. The measuring system of claim 1, wherein the meter comprises a first speed of sound sensor arranged on the outward portion of the tube and a second speed of sound sensor arranged on the inward portion of the tube for determining the speed of sound measurement on the fluid flowing in each respective inward and outward portion of the tube.

4. The measuring system of claim 1, wherein the meter comprises a first speed of sound sensing device arranged on the pipe at the input end of the meter and a second speed of sound sensing device arranged of the pipe at the output end of the meter for performing the speed of sound measurement of the fluid flowing therethrough.

5. The measuring device of claim 1, wherein the tubes are bent or straight.

6. The measuring system meter of claim 1, wherein the meter comprises at least one tube having a first array of sensors arranged on the outward portion of the tube and a second array of sensors arranged on the inward portion of the tube for determining the speed of sound measurement on the fluid flowing in each respective inward and outward portion of the tube.

7. The measuring system of claim 6, wherein the array of sensors includes strain based sensors.

8. A method for measuring the mass flow rate of an aerated fluid flowing in a pipe, the method comprising:

vibrating a pair of tubes having the fluid flowing therethrough, said tubes having an inward flow portion and an outward flow portion;

measuring a phase signal indicative of a phase difference between a pair of tubes;

measuring the speed of sound propagating through the fluid at the inward flow portion and outward flow portion of a tube;

providing at least one of a SOS signal indicative of the speed of sound propagating through the fluid, a GVF signal indicative of the gas volume fraction of the fluid, and a reduced frequency indicative of the reduced frequency of the fluid; and determining a compensated mass flow rate measurement in response to at least one of the SOS signal, the GVF signal and the reduced frequency signal and the phase signal.

9. The method of claim 8, further includes determining wherein a gas volumetric fraction (GVF) in the flow of the fluid in response to the SOS signal.

10. The method of claim 8, wherein the measuring the speed of sound includes providing a first speed of sound sensor arranged on the outward portion of the tube and a second speed of sound sensor arranged on the inward portion of the tube for determining the speed of sound measurement on the fluid flowing in each respective inward and outward portion of the tube.

11. The method of claim 8, wherein the measuring the speed of sound includes providing a first speed of sound sensing device arranged on the pipe at the input end of the meter and a second speed of sound sensing device arranged of the pipe at the output end of the meter for performing the speed of sound measurement of the fluid flowing therethrough.

12. The method claim 8, wherein the tubes are bent or straight.

13. The method of claim 8, wherein measuring the speed of sound includes providing at least one tube having a first array of sensors arranged on the outward portion of the tube and a second array of sensors arranged on the inward portion of the tube for determining the speed of sound measurement on the fluid flowing in each respective inward and outward portion of the tube.

14. The method of claim 13, wherein the array of sensors includes strain based sensors.

* * * * *